United States Patent
Nozawa et al.

(10) Patent No.: US 12,201,446 B2
(45) Date of Patent: Jan. 21, 2025

(54) STRESS COPING STYLE DETERMINATION SYSTEM, STRESS COPING STYLE DETERMINATION METHOD, LEARNING DEVICE, LEARNING METHOD, PROGRAM, AND LEARNED MODEL

(71) Applicant: KOSENSHA CO., LTD., Tokyo (JP)

(72) Inventors: Akio Nozawa, Tokyo (JP); Kosuke Oiwa, Sagamihara (JP); Kenichi Nakano, Tokyo (JP)

(73) Assignee: KOSENSHA CO., LTD., Tokyo (JP)

( * ) Notice: Subject to any disclaimer, the term of this patent is extended or adjusted under 35 U.S.C. 154(b) by 287 days.

(21) Appl. No.: 17/638,944

(22) PCT Filed: Aug. 28, 2020

(86) PCT No.: PCT/JP2020/032763
§ 371 (c)(1),
(2) Date: Feb. 28, 2022

(87) PCT Pub. No.: WO2021/040025
PCT Pub. Date: Mar. 4, 2021

(65) Prior Publication Data
US 2022/0296162 A1    Sep. 22, 2022

(30) Foreign Application Priority Data

Aug. 30, 2019   (JP) .................................. 2019-158134
Aug. 28, 2020   (JP) .................................. 2020-144666

(51) Int. Cl.
*A61B 5/00*     (2006.01)
*A61B 5/02*     (2006.01)
(Continued)

(52) U.S. Cl.
CPC ........ *A61B 5/4884* (2013.01); *A61B 5/02007* (2013.01); *A61B 5/02055* (2013.01);
(Continued)

(58) Field of Classification Search
CPC .............. A61B 5/4884; A61B 5/02007; A61B 5/02055; A61B 5/029; A61B 5/7264;
(Continued)

(56) References Cited

U.S. PATENT DOCUMENTS

2016/0100766 A1*  4/2016  Yoshioka ............. A61B 5/0082
                                                    600/301
2018/0228447 A1*  8/2018  Arai ..................... G06V 40/174
(Continued)

FOREIGN PATENT DOCUMENTS

JP    H06-054836 A    3/1994
JP    2007-068620 A   3/2007

OTHER PUBLICATIONS

Asano, "Stress Presumption of the Long Driving Using the Facial Thermal Image", Journal of Robotics and Mechatronics vol. 22 No. 6, 2010. (Year: 2010).*

(Continued)

*Primary Examiner* — Juan A Torres
(74) *Attorney, Agent, or Firm* — Locke Lord LLP

(57) ABSTRACT

Provided is a system capable of determining a stress coping style of a test subject in a non-contact state. The system includes a biological information acquiring part which acquires biological information of a test subject in a non-contact state, and a determining part which determines a stress coping style of the test subject based on the biological information and a response pattern specified in advance. The response pattern is specified by a hemodynamic parameter.

21 Claims, 42 Drawing Sheets

(51) Int. Cl.
  *A61B 5/0205* (2006.01)
  *A61B 5/029* (2006.01)
  *G06V 10/77* (2022.01)
  *G06V 10/776* (2022.01)
  *G06V 40/16* (2022.01)
  *A61B 5/021* (2006.01)
  *A61B 5/024* (2006.01)

(52) U.S. Cl.
  CPC ............ *A61B 5/029* (2013.01); *A61B 5/7264* (2013.01); *G06V 10/7715* (2022.01); *G06V 10/776* (2022.01); *G06V 40/171* (2022.01); *G06V 40/172* (2022.01); *A61B 5/021* (2013.01); *A61B 5/024* (2013.01)

(58) Field of Classification Search
  CPC .... A61B 5/021; A61B 5/024; G06V 10/7715; G06V 10/776; G06V 40/171; G06V 40/172; G06V 10/454; G06V 10/143; G06V 10/469
  USPC ......................................................... 382/128
  See application file for complete search history.

(56) References Cited

U.S. PATENT DOCUMENTS

2019/0059799 A1* 2/2019 Arai ..................... A61B 5/015
2019/0328246 A1* 10/2019 Wu ....................... A61B 5/024

OTHER PUBLICATIONS

H. Asano et al., "Stress Evaluation while Prolonged Driving Operation Using the Facial Skin Temperature," T. SICE, vol. 47, No. 1, Jan. 2011, pp. 2-7 and English abstract thereof. (cited in the ISR).

A. Nozawa et al., "Estimation Method of Information Understanding in Communication by Nasal Skin Thermogram," IEEJ Trans, FM, vol. 126, No. 9, 2006, pp. 909-914, Englsih Extended Summary and English abstract thereof. (cited in the ISR).

T. Watanuki et al., "Estimation of Mode of Viewing TV and Preference of TV Contents by Autonomic Nervous System Index," IEEJ Trans. EIS, vol. 134, No. 10, 2014, pp. 1551-1556 and English abstract thereof. (cited in the ISR).

\* cited by examiner

Fig. 5

|  | MBP | HR | CO | TPR |
|---|---|---|---|---|
| PATTERN I | + | + | + | / |
| PATTERN II | + | / | / | + |

Fig. 10

|  | SIZE | STRIDE | COUNT |
|---|---|---|---|
| FIRST LAYER | 2 × 2 | 4 | 48 |
| SECOND LAYER | 2 × 2 | 4 | 96 |
| THIRD LAYER | 2 × 2 | 4 | 192 |

Fig. 11

|  | SIZE | STRIDE |
|---|---|---|
| FIRST LAYER | 4 × 4 | 4 |
| SECOND LAYER | 4 × 4 | 4 |
| THIRD LAYER | 4 × 4 | 4 |

Fig. 12
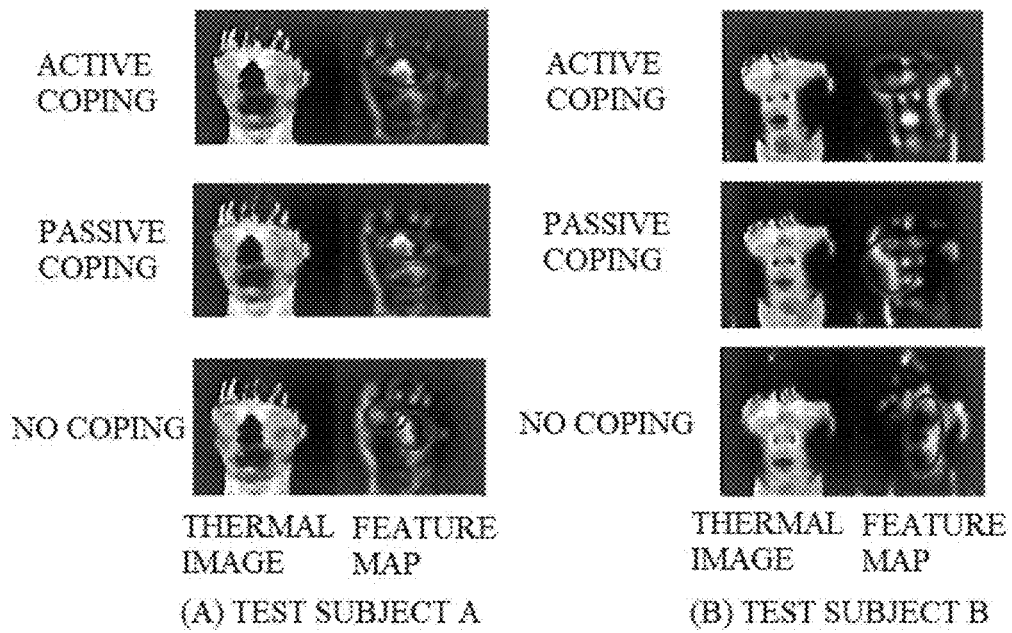
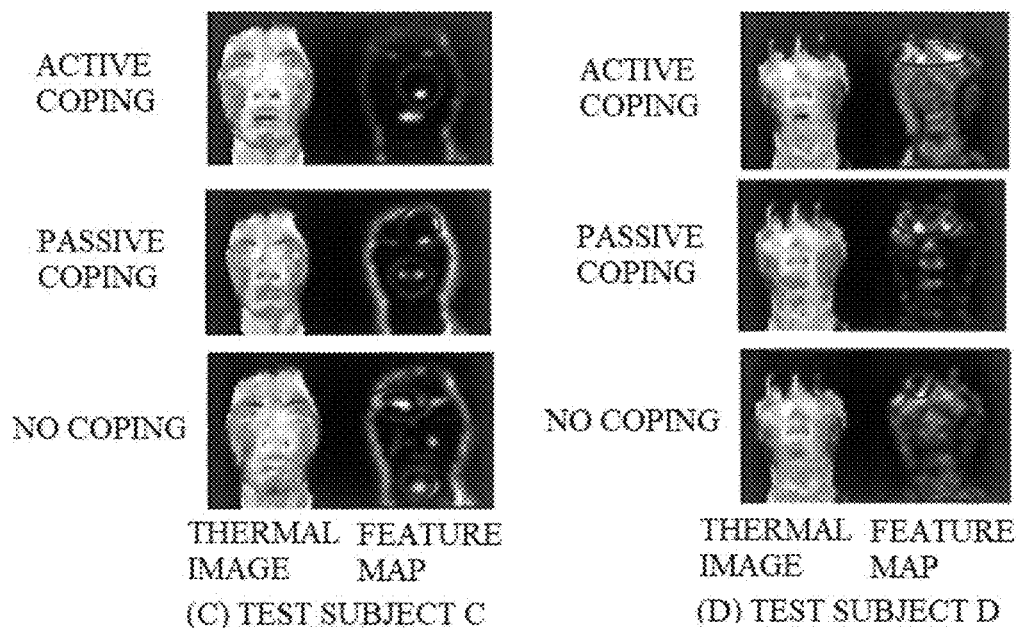

Fig. 13

| R1 | Watch TV contents | R2 |
|---|---|---|
| 1min | 5min | 1min |

Measurement →

Fig. 16

| MMS | before | after | p-value |
|---|---|---|---|
| D-A | 7.86 ± 0.67 | 7.13 ± 0.73 | n.s. |
| H | 6.60 ± 0.63 | 5.46 ± 0.20 | n.s. |
| F | 9.06 ± 1.03 | 7.33 ± 0.55 | + $p < 0.1$ |
| A | 9.13 ± 0.85 | 9.66 ± 0.72 | + $p < 0.1$ |
| I | 10.1 ± 1.02 | 9.06 ± 0.78 | n.s. |
| AF | 6.46 ± 0.51 | 9.00 ± 0.93 | ** $p < 0.01$ |
| D | 7.26 ± 0.78 | 7.00 ± 0.68 | n.s. |
| S | 5.80 ± 0.40 | 6.80 ± 0.63 | n.s. |

Fig. 17

| MMS | before | after | p-value |
|---|---|---|---|
| D-A | 6.66 ± 0.60 | 7.13 ± 0.63 | n.s. |
| H | 5.53 ± 0.36 | 7.40 ± 0.58 | ** $p < 0.01$ |
| F | 8.66 ± 0.69 | 13.8 ± 0.86 | ** $p < 0.01$ |
| A | 7.20 ± 0.62 | 6.40 ± 0.57 | n.s. |
| I | 8.86 ± 0.70 | 7.93 ± 0.92 | n.s. |
| AF | 6.33 ± 0.51 | 6.06 ± 0.42 | n.s. |
| D | 7.13 ± 0.57 | 7.13 ± 0.68 | n.s. |
| S | 5.66 ± 0.39 | 6.40 ± 0.61 | n.s. |

Fig. 18

| MMS | before | after | p-value |
|---|---|---|---|
| D-A | 6.90 ± 0.66 | 9.72 ± 1.01 | * $p < 0.05$ |
| H | 5.81 ± 0.44 | 10.1 ± 1.48 | * $p < 0.05$ |
| F | 9.54 ± 0.67 | 8.54 ± 0.77 | n.s. |
| A | 7.00 ± 0.70 | 6.00 ± 0.49 | + $p < 0.1$ |
| I | 7.63 ± 0.63 | 5.36 ± 0.19 | ** $p < 0.01$ |
| AF | 6.00 ± 0.48 | 5.36 ± 0.34 | n.s. |
| D | 6.63 ± 0.59 | 8.63 ± 1.03 | * $p < 0.05$ |
| S | 6.36 ± 0.67 | 14.5 ± 1.52 | ** $p < 0.01$ |

Fig. 19

| MMS | before | after | p-value |
|---|---|---|---|
| D-A | 7.50 ± 1.63 | 9.25 ± 2.80 | n.s. |
| H | 5.00 ± 0.00 | 7.25 ± 1.24 | n.s. |
| F | 10.0 ± 1.45 | 13.7 ± 3.16 | n.s. |
| A | 6.25 ± 0.81 | 5.00 ± 0.00 | n.s. |
| I | 6.25 ± 0.41 | 5.00 ± 0.00 | + $p < 0.1$ |
| AF | 5.25 ± 0.21 | 5.00 ± 0.00 | n.s. |
| D | 7.00 ± 1.22 | 6.25 ± 0.54 | n.s. |
| S | 5.00 ± 0.00 | 16.2 ± 0.64 | ** $p < 0.01$ |

Fig. 20

| VAS | before | after | p-value |
|---|---|---|---|
| Comfortable | 0.50 ± 0.04 | 0.62 ± 0.02 | ** $p < 0.01$ |
| Arousal | 0.41 ± 0.05 | 0.55 ± 0.04 | ** $p < 0.01$ |
| Vigor | 0.49 ± 0.05 | 0.58 ± 0.03 | + $p < 0.1$ |
| Preference | | 0.70 ± 0.03 | |
| Concentration | | 4.21 ± 0.10 | |

※ Diagonal line represents data does not exist.

Fig. 21

| VAS | before | after | p-value |
|---|---|---|---|
| Comfortable | 0.54 ± 0.04 | 0.40 ± 0.04 | ** $p < 0.01$ |
| Arousal | 0.52 ± 0.04 | 0.33 ± 0.06 | ** $p < 0.01$ |
| Vigor | 0.48 ± 0.04 | 0.34 ± 0.05 | * $p < 0.05$ |
| Preference | | 0.31 ± 0.04 | |
| Concentration | | 1.73 ± 0.19 | |

※ Diagonal line represents data does not exist.

Fig. 22

| VAS | before | after | p-value |
|---|---|---|---|
| Comfortable | 0.55 ± 0.05 | 0.37 ± 0.06 | + $p < 0.1$ |
| Arousal | 0.50 ± 0.06 | 0.74 ± 0.05 | ** $p < 0.01$ |
| Vigor | 0.47 ± 0.05 | 0.36 ± 0.05 | + $p < 0.1$ |
| Preference |  | 0.31 ± 0.07 |  |
| Concentration |  | 4.72 ± 0.13 |  |

※ Diagonal line represents data does not exist.

Fig. 23

| VAS | before | after | p-value |
|---|---|---|---|
| Comfortable | 0.52 ± 0.02 | 0.29 ± 0.09 | n.s. |
| Arousal | 0.38 ± 0.07 | 0.68 ± 0.12 | n.s. |
| Vigor | 0.45 ± 0.03 | 0.35 ± 0.10 | n.s. |
| Preference | | 0.21 ± 0.09 | |
| Concentration | | 1.75 ± 0.21 | |

※ Diagonal line represents data does not exist.

Fig. 25

|  | Positive | Negative | Horror(C) | Horror(N) |
|---|---|---|---|---|
| NST | N** | N** | n.s. | N** |
| Alpha-wave | n.s. | n.s. | n.s. | n.s. |
| HF | n.s. | N** | N** | P** |
| MP | P** | n.s. | P** | P** |
| HR | P** | N** | P* | n.s. |
| SV | P** | P** | P** | P** |
| CO | P** | P** | P** | P** |
| TPR | N** | N** | N** | P** |

Fig. 30

| | Preference | Stress coping style | Excitement-Calm |
|---|---|---|---|
| feature vector | slope of unit time intervals in heart rate | slope of unit time intervals in hemodynamic parameter | slope of 30-second intervals in hemodynamic parameter |
| The number of input layer | 30 | 30 | 30 |
| The number of middle layer | 16 | 16 | 16 |
| The number of output layer | 2 | 3 | 1 |
| instruction signal | Positive Negative | Active coping Passive coping No stress coping | Value of Excitement-Calm |

Fig. 32

|  | Positive | Negative | Horro(C) | Horror(N) |
|---|---|---|---|---|
| Comfortable | 0.13 ± 0.04** | -0.16 ± 0.03** | -0.18 ± 0.08+ | -0.23 ± 0.10 |
| Arousal | 0.15 ± 0.05** | -0.23 ± 0.05** | 0.24 ± 0.07** | 0.30 ± 0.16 |
| Vigor | 0.09 ± 0.06+ | -0.17 ± 0.04* | -0.11 ± 0.05+ | -0.10 ± 0.09 |
| Preference | 0.70 ± 0.03 | 0.31 ± 0.04 | 0.31 ± 0.07 | 0.21 ± 0.09 |
| Concentration | 4.21 ± 0.10 | 1.73 ± 0.19 | 4.72 ± 0.13 | 1.75 ± 0.21 |

※ P-Value : ** $p < 0.01$, * $p < 0.05$, + $p < 0.1$

Fig. 33

|     | Positive | Negative | Horro(C) | Horror(N) |
|-----|----------|----------|----------|-----------|
| MP  | P**      | n.s.     | P**      | P**       |
| HR  | P**      | N**      | P*       | n.s.      |
| SV  | P**      | P**      | P**      | P**       |
| CO  | P**      | P**      | P**      | P**       |
| TPR | N**      | N**      | N**      | P**       |

※ P-Value : ** $p < 0.01$, * $p < 0.05$, + $p < 0.1$

Fig. 34

| Unit time[s] | Distinction rate of preference[%] | Distinction rate of mode of viewing[%] |
|---|---|---|
| 10 | 79.2 | 50 |
| 20 | 75 | 54.2 |
| 30 | 75 | 58.3 |
| 40 | 70.8 | 66.7 |
| 50 | 83.3 | 75 |
| 60 | 75 | 62.5 |

STRESS COPING STYLE DETERMINATION SYSTEM, STRESS COPING STYLE DETERMINATION METHOD, LEARNING DEVICE, LEARNING METHOD, PROGRAM, AND LEARNED MODEL

TECHNICAL FIELD

The present invention relates to technologies for determining a stress coping style of a test subject in a non-contact state.

BACKGROUND ART

Techniques for grasping a stress state of a test subject have been publicly known. For example, Patent Literature 1 describes a technique for estimating a psychological change of a test subject by measuring an amount of heat of facial thermal radiation.

Also, Patent Literature 2 describes a technique of performing a level measurement of a psychological state of a test subject based on facial image information. According to these techniques, some psychological change in the test subject can be detected in a non-contact state, and the psychological state of the test subject can be quantitatively analyzed in a non-contact state.

However, in the techniques of Patent Literatures 1 and 2, since the type of stress being felt by the test subject cannot be known, qualitative analysis on stress of the test subject cannot be performed.

CITATION LIST

Patent Literatures

PTL 1: Japanese Unexamined Patent Application Publication No. 6-54836
PTL 2: Japanese Unexamined Patent Application Publication No. 2007-68620

SUMMARY OF INVENTION

Technical Problem

Meanwhile, it has been known that, in order for the cardiovascular system to satisfy metabolic demands from the respective tissues of the body when facing a stress stimulus, the human exhibits any one of characteristic reaction patterns. That is, these are a pattern indicating active coping, a pattern indicating passive coping, and a pattern of not performing any particular coping against stress. These are referred to as "stress coping styles". When the pattern of active coping is exhibited, that test subject can be presumed to be in a good stress state. By contrast, when the pattern of passive coping is exhibited, that test subject can be presumed to be in a bad stress state.

That is, by determining a stress coping style of the test subject, it is possible to grasp the type of stress being felt by the test subject.

The present invention provides a stress coping style determination system, stress coping style determination method, learning device, and learning method capable of determining a stress coping style of a test subject in a non-contact state, and a program and learned model for achieving these by using a computer.

Solution to Problem

To solve the above-described problem, a stress coping style determination system is to have a biological information acquiring part which acquires biological information of a test subject in a non-contact state and a determining part which determines a stress coping style of the test subject based on the biological information and a response pattern specified in advance, in which the response pattern is specified by a hemodynamic parameter, in accordance with an embodiment.

This stress coping style determination system acquires the biological information of the test subject in the non-contact state, and determines the stress coping style of that test subject based on that biological information and the response pattern specified by the hemodynamic parameter in the non-contact state.

Also, in an embodiment of the stress coping style determination system, the hemodynamic parameter includes a plurality of parameters among a mean blood pressure, a heart rate, a cardiac output, a stroke volume, and a total peripheral resistance.

Here, "hemodynamics" means one branch of cardiovascular physiology as for blood circulation, and is a study field with the theories of dynamics, elastic body dynamics, and fluid dynamics applied to the biological system.

Specifically, studied in hemodynamics are: intracardiac pressure, heart beat, workload, and output of the heart; elasticity of blood vessels and cardiac muscle; pulse; blood flow velocity; blood viscosity; and so forth. Therefore, "hemodynamic parameters" in the present invention refer to parameters of numerical values such as intracardiac pressure, heart beat, workload, and output of the heart, elasticity of blood vessels and cardiac muscle, pulse, blood flow velocity, blood viscosity, and so forth.

This stress coping style determination system acquires the biological information of the test subject in the non-contact state, and determines the stress coping style of that test subject based on that biological information and the response pattern specified by the plurality of parameters among the mean blood pressure, the heart rate, the cardiac output, the stroke volume, and the total peripheral resistance. Also, the hemodynamic parameter can be identified by a continuous blood-pressure meter in general.

Also, in an embodiment of the stress coping style determination system, the biological information is a facial image.

This stress coping style determination system acquires the facial image of the test subject in the non-contact state, and determines the stress coping style of that test subject based on that facial image and the response pattern.

Also, in an embodiment of the stress coping style determination system, the facial image is a facial thermal image or a facial visible image.

This stress coping style determination system acquires the facial thermal image or facial visible image of the test subject in the non-contact state, and determines the stress coping style of that test subject based on that facial thermal image or facial visual image and the response pattern.

In this case, the "facial visible image" is an image acquired by taking an image of the facial surface of the test subject with a camera widely used in general, that is, a device having an optical system for image formation to take an image. In this case, a color image is preferable. Also, the "facial thermal image" is an image acquired by analyzing infrared rays emitted from the facial surface of the test subject and presenting a thermal distribution as a drawing, and is acquired by taking an image with infrared thermography.

Also, in an embodiment of the stress coping style determination system, the determining part determines the stress coping style of the test subject by observing a stress response of a specific region of a facial surface including in the facial image.

This stress coping style determination system determines the stress coping style of that test subject based on the stress response of the specific region of the facial surface of the test subject and the response pattern.

Also, in an embodiment, the stress coping style determination system is that the response pattern includes patterns of three types formed of "active coping", "passive coping", and "no coping".

This stress coping style determination system acquires the biological information of the test subject in the non-contact state, and determines that the stress coping style of that test subject based on that biological information is any response pattern among "active coping", "passive coping", and "no coping".

Also, in an embodiment of the stress coping style determination system, the determining part has a determination-purpose feature value storage part which has stored therein a spatial feature value corresponding to "active coping", a spatial feature value corresponding to "passive coping", and a spatial feature value corresponding to "no coping" and the determining part determines that the stress coping style is any response pattern among "active coping", "passive coping", and "no coping", based on the biological information and the respective spatial feature values stored in the determination-purpose feature value storage part.

This stress coping style determination system stores a spatial feature value corresponding to "active coping", a spatial feature value corresponding to "passive coping", and a spatial feature value corresponding to "no coping" and determines that the stress coping style of that test subject is any response pattern among "active coping", "passive coping", and "no coping", based on the biological information of the test subject and the respective spatial feature values.

Also, in an embodiment of the stress coping style determination system, the spatial feature values stored in the determination-purpose feature value storage part are spatial feature values extracted by a machine learning part, and the machine learning part has a learning data storage part which has stored therein a plurality of learning-purpose facial images labelled so as to correspond to "active coping", "passive coping", and "no coping", respectively, a feature value extracting part which extracts a spatial feature value of the facial image from the learning-purpose facial images by using a learned model, and a feature value learning part which changes a network parameter of the learned model so that extraction accuracy of the spatial feature value by the feature value extracting part is enhanced, based on a relation between the extraction result by the feature value extracting part and a label provided to the learning-purpose facial image as an extraction target.

This stress coping style determination system extracts, by the machine learning part, a spatial feature value corresponding to "active coping", a spatial feature value corresponding to "passive coping", and a spatial feature value corresponding to "no coping".

The machine learning part has stored therein the plurality of learning-purpose facial images labelled so as to correspond to "active coping", "passive coping", and "no coping", respectively, extracts the spatial feature value of the facial image of the test subject from the learning-purpose facial images by using the learned model, and changes the network parameter of the learned model so that extraction accuracy of the spatial feature value of the facial image of the test subject is enhanced, based on the relation between that extraction result and the label provided to the learning-purpose facial image as the extraction target.

Also, in an embodiment of the stress coping style determination system, the spatial feature value is a fractal dimension calculated based on the facial image of the test subject.

Also, in an embodiment, a program is a program for causing a computer to function as means of determining a stress coping style of a test subject, the program having a determination-purpose feature value storing step of storing a spatial feature value corresponding to "active coping", a spatial feature value corresponding to "passive coping", and a spatial feature value corresponding to "no coping", and a determining step of determining whether the stress coping style of the test subject is any response pattern among "active coping", "passive coping", and "no coping", based on a facial image of the test subject and the respective spatial feature values stored at the determination-purpose feature value storing step, wherein the response pattern is specified by a hemodynamic parameter.

Installed in and executed by one or a plurality of computers mutually working in coordination, this program causes a system formed of one or the plurality of computers to function as means of determining that the stress coping style of the test subject is any response pattern among "active coping", "passive coping", and "no coping", based on the spatial feature value corresponding to "active coping", the spatial feature value corresponding to "passive coping", and the spatial feature value corresponding to "no coping", and the facial image of the test subject.

Also, in an embodiment, the program has a learning data storing step of storing a plurality of learning-purpose facial images labelled so as to correspond to "active coping", "passive coping", and "no coping", respectively, a feature value extracting step of extracting a spatial feature value of the learning-purpose facial image by using a learned model, and a learning step of changing a network parameter of the learned model so that extraction accuracy of the spatial feature value at the feature value extracting step is enhanced, based on a relation between the extraction result at the feature value extracting step and a label provided to the learning-purpose facial image as an extraction target, and the determination-purpose feature value storing step is a step of storing the spatial feature value extracted at the feature value extracting step.

Installed in and executed by one or a plurality of computers mutually working in coordination, this program causes a system formed of one or the plurality of computers to function as means of storing the plurality of learning-purpose facial images labelled so as to correspond to "active coping", "passive coping", and "no coping", respectively, extracting the spatial feature value of the learning-purpose facial image by using the learned model, changing the network parameter of the learned model so that extraction accuracy of the spatial feature value is enhanced, based on the relation between that extraction result and the label provided to the learning-purpose facial image as the extraction target, and also storing the extracted spatial feature value.

Also, in an embodiment of the program, the spatial feature value is a fractal dimension calculated based on the facial image of the test subject.

Also, in an embodiment, a stress coping style determination method is to have a biological information acquiring step of acquiring biological information of a test subject in a non-contact state and a determining step of determining a stress coping style of the test subject based on the biological information and a response pattern specified in advance, wherein the response pattern is specified by a hemodynamic parameter.

This stress coping style determination method acquires the biological information of the test subject in the non-contact state, and determines the stress coping style of that test subject based on that biological information and the response pattern specified by the hemodynamic parameter.

Also, in an embodiment, a learning device is to have a learning data storage part which has stored therein a plurality of learning-purpose facial images labelled so as to each correspond to a response pattern specified by a hemodynamic parameter, a feature value extracting part which extracts a spatial feature value of a facial image of a test subject from the learning-purpose facial images by using a learned model, and a feature value learning part which changes a network parameter of the learned model so that extraction accuracy of the spatial feature value by the feature value extracting part is enhanced, based on a relation between the extraction result at the feature value extracting part and a label provided to the learning-purpose facial image as an extraction target.

This learning device stores the plurality of learning-purpose facial images labelled so as to each correspond to the response pattern specified by the hemodynamic parameter, extracts the spatial feature value of the facial image of the test subject from the learning-purpose facial images by using the learned model, and changes the network parameter of the learned model so that extraction accuracy of the spatial feature value of the facial image of the test subject is enhanced, based on the relation between that extraction result and the label provided to the learning-purpose facial image as the extraction target.

Also, in an embodiment of the learning device, the spatial feature value is a fractal dimension calculated based on the facial image of the test subject.

Also, in an embodiment, a learning method is characterized to have a learning data storing step of storing a plurality of learning-purpose facial images labelled so as to each correspond to a response pattern specified by a hemodynamic parameter, a feature value extracting step of extracting a spatial feature value of a facial image of a test subject from the learning-purpose facial images by using a learned model, a feature value learning step of changing a network parameter of the learned model so that extraction accuracy of the spatial feature value by the feature value extracting step is enhanced, based on a relation between the extraction result at the feature value extracting step and a label provided to the learning-purpose facial image as an extraction target.

This learning method stores the plurality of learning-purpose facial images labelled so as to each correspond to the response pattern specified by the hemodynamic parameter, extracts the spatial feature value of the facial image of the test subject from the learning-purpose facial images by using the learned model, and changes the network parameter of the learned model so that extraction accuracy of the spatial feature value of the facial image of the test subject is enhanced, based on the relation between that extraction result and the label provided to the learning-purpose facial image as the extraction target.

Also, in an embodiment of the learning method, the spatial feature value is a fractal dimension calculated based on the facial image of the test subject.

Also, in an embodiment, a program is a program for causing a computer to function as means of learning a spatial feature value of a facial image, the program is to have a learning data storing step of storing a plurality of learning-purpose facial images labelled so as to each correspond to a response pattern specified by a hemodynamic parameter, a feature value extracting step of extracting a spatial feature value of the facial image of a test subject from the learning-purpose facial images by using a learned model, and a feature value learning step of changing a network parameter of the learned model so that extraction accuracy of the spatial feature value by the feature value extracting step is enhanced, based on a relation between the extraction result at the feature value extracting step and a label provided to the learning-purpose facial image as an extraction target.

Installed in and executed by one or a plurality of computers mutually working in coordination working in coordination, this program causes a system formed of one or the plurality of computers to function as means of storing the plurality of learning-purpose facial images labelled so as to each correspond to the response pattern specified by the hemodynamic parameter, extracting the spatial feature value of the facial image of the test subject from these learning-purpose facial images by using the learned model, changing the network parameter of the learned model so that extraction accuracy of the spatial feature value of the facial image of the test subject is enhanced, based on the relation between that extraction result and the label provided to the learning-purpose facial image as the extraction target.

Also, in an embodiment of the program, the spatial feature value is a fractal dimension calculated based on the facial image of the test subject.

Also, in an embodiment, a learned model is to be generated by machine-learning a spatial feature value of a facial image of a test subject by using a plurality of learning-purpose facial images labelled so as to each correspond to a response pattern specified by a hemodynamic parameter as teacher data.

This learned model takes the facial image of the test subject as an input and the spatial feature value of the facial image of the test subject as an output.

Also, in an embodiment, the learned model is that, in the program, the spatial feature value is a fractal dimension calculated based on the facial image of the test subject.

Advantageous Effects of Invention

According to an embodiment of the stress coping style determination system, the biological information of the test subject is acquired in a non-contact state, and the stress coping style of that test subject can be determined in a non-contact state based on that biological information and the response pattern specified by the hemodynamic parameter. Thus, it is possible to grasp the type of stress being felt by the test subject without imposing constraints on the behavior of the test subject.

While a term "stress" is widely used in general, "stress" is psychologically defined as "a general term of nonspecific reactions occurring against a stimulus (stressor) from outside acting on a living body" (psychologist Dr. Hans Selye).

Based on human survival, various stressors exist. It has been known that, particularly in recent years, there are many stressors in social environments, which have been exerting various effects on the living body. In some cases, it has been medically revealed that these stressors may cause a disease.

However, not all stresses are bad for human existence. Even if suffering stress, it has been known that the living body is activated if trying to cope with stress and a plus effect may be brought. From this point of view, Dr. Selye has revealed that stress can become good stress (enstress) or bad stress (distress) depending on the difference in biological conditions on the suffering side, the degree of stress, and so forth.

Therefore, from this viewpoint of psychology, when stress is considered, all stresses in general should not be considered as bad, and it is required to think them by classifying the types of stress for the living body as described above. Also, with this point of view, it is possible to socially, industrially, and positively think how stress is managed in various present-day social activities and how, for example, production efficiency and working efficiency, are increased.

However, as described above, while techniques and patented inventions for grasping a stress state of a test subject have been publicly known, according to these conventional schemes, stress being felt by the test subject cannot be generally grasped, and qualitative analysis based on the type of stress being felt by the test subject cannot be performed.

According to the invention of the present application, by classifying and grasping the types of stress in accordance with the test subject, a relation between a stressor and a stress reaction by the test subject can be grasped in more detail. As a result, a relationship between social environments and so forth as a stressor and the human can be more correctly analyzed and studied, and the results can be applied to various fields of social environments to solve problems. Also, they can be applied to various industrial fields to improve production efficiency and promote industrial activities.

According to an embodiment of the stress coping style determination system, the stress coping style of that test subject can be correctly determined in detail based on the biological information and the response pattern specified by any of the mean blood pressure, the heart rate, the cardiac output, the stroke volume, and the total peripheral resistance of the test subject.

According to an embodiment of the stress coping style determination system, the facial image of the test subject is acquired in a non-contact state, and the stress coping style of that test subject can be quickly determined based on that facial image and the response pattern specified by the hemodynamic parameter without constraining or putting a physical burden on the test subject, unlike the conventional case of using a continuous blood-pressure meter.

According to an embodiment of the stress coping style determination system, the facial thermal image or facial visible image of the test subject is acquired in a non-contact state, and the stress coping style of that test subject can be determined based on psychophysiology based on the facial thermal image or facial visible image and the response pattern specified by the hemodynamic parameter.

According to an embodiment of the stress coping style determination system, based on the state of the specific region of the facial surface of the test subject and the response pattern specified by the hemodynamic parameter, the stress coping style of that test subject can be easily and correctly determined.

According to an embodiment of the stress coping style determination system, the biological information of the test subject is acquired in a non-contact state and, based on that biological information, it can be determined that the stress coping style of that test subject is a style indicating any response pattern among "active coping", "passive coping", and "no coping".

Therefore, since the stress coping styles can be classified into response patterns of three types: "active coping", "passive coping", and "no coping", analysis is performed based on this response pattern, and the analysis result is applied to personnel administration tasks, quality control tasks, and so forth of various industrial fields. This can contribute to an improvement in quality of various tasks.

According to an embodiment of the stress coping style determination system, the spatial feature value corresponding to "active coping", the spatial feature value corresponding to "passive coping", and the spatial feature value corresponding to "no coping" are stored and, based on the biological information of the test subject and each spatial feature value, it can be determined that the stress coping style of that test subject is a style indicating any response pattern among "active coping", "passive coping", and "no coping".

According to an embodiment of the stress coping style determination system, the network parameter of the learned model can be changed so that extraction accuracy of the spatial feature value of the facial image of the test subject is enhanced.

According to an embodiment of the stress coping style determination system, since the spatial feature value can be accurately converted into numbers by a fractal dimension, the stress coping style of the test subject can be accurately determined in a non-contact state.

According to an embodiment of the program, by using one or a plurality of computers mutually working in coordination, it is possible to achieve a system which determines that the stress coping style of the test subject is any response pattern among "active coping", "passive coping", and "no coping" based on the spatial feature value corresponding to "active coping", the spatial feature value corresponding to "passive coping", and the spatial feature value corresponding to "no coping" and the facial image of the test subject.

According to an embodiment of the program, by using one or a plurality of computers mutually working in coordination, it is possible to achieve a system which stores the plurality of learning-purpose facial images labelled so as to correspond to "active coping", "passive coping", and "no coping", respectively, extracts the spatial feature value of the learning-purpose facial image by using the learned model, changes the network parameter of the learned model so that extraction accuracy of the spatial feature value is enhanced, based on the relation between that extraction result and the label provided to the learning-purpose facial image as the extraction target, and stores the extracted spatial feature value.

According to an embodiment of the program, since the spatial feature value can be accurately converted into numbers by a fractal dimension, by using one or a plurality of computers mutually working in coordination, it is possible to achieve a system capable of more accurately determining the stress coping style of the test subject in a non-contact state.

According to an embodiment of the stress coping style determination method, the biological information of the test subject is acquired in a non-contact state and the stress coping style of that test subject can be determined in a non-contact state based on that biological information and the response pattern specified by the hemodynamic parameter. Thus, it is possible to grasp the type of stress being felt by the test subject without imposing constraints on the behavior of the test subject.

According to an embodiment of the learning device, the network parameter of the learned model can be changed so that extraction accuracy of the spatial feature value of the facial image of the test subject is enhanced.

According to an embodiment of the learning device, since the spatial feature value can be accurately converted into numbers by a fractal dimension, the network parameter of the learned model can be changed so that extraction accuracy of the spatial feature value of the facial image of the test subject is enhanced more.

According to an embodiment of the learning method, the network parameter of the learned model can be changed so that extraction accuracy of the spatial feature value of the facial image of the test subject is enhanced.

According to an embodiment of the learning method, since the spatial feature value can be accurately converted into numbers by a fractal dimension, the network parameter of the learned model can be changed so that extraction accuracy of the spatial feature value of the facial image of the test subject is enhanced more.

According to an embodiment of the program, installing this program on one or a plurality of computers mutually working in coordination and executing the program achieves a learning device which changes the network parameter of the learned model so that extraction accuracy of the spatial feature value of the facial image of the test subject is enhanced.

According to an embodiment of the program of, since the spatial feature value can be accurately converted into numbers by a fractal dimension, installing this program on one or a plurality of computers mutually working in coordination and executing the program, achieves a learning device which changes the network parameter of the learned model so that extraction accuracy of the spatial feature value of the facial image of the test subject is enhanced more.

According to an embodiment of the learned model, by inputting the facial image of the test subject into this, it is possible to extract the spatial feature value of the facial image of that test subject.

According to an embodiment of the learned model, since the spatial feature value can be accurately converted into numbers by a fractal dimension, by inputting the facial image of the test subject into this learned model, it is possible to accurately extract the spatial feature value of the facial image of that test subject.

BRIEF DESCRIPTION OF DRAWINGS

Figure 5:
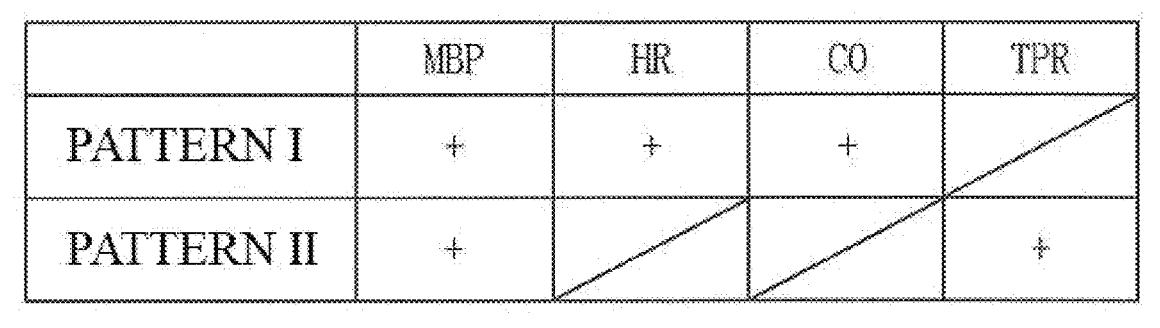

FIG. 5 is a table illustrating hemodynamic pattern reactions of a previous research of Experiment Example 1.

FIG. 10 is a table representing a filter size, stride, and the number of filters of each convolutional layer.

FIG. 11 is a table representing a filter size and stride of a pooling layer.

FIG. 12 is a diagram illustrating a feature of a face in each of cases of active coping, passive coping, and no coping of each test subject in comparison of a heat image and a feature map of the face.

FIG. 13 is a conceptual diagram illustrating an experiment protocol of Experiment Example 2.

FIG. 16 is a table illustrating variations in multiple mental scales for "Positive" contents.

FIG. 17 is a table illustrating variations in multiple mental scales for "Negative" contents.

FIG. 18 is a table illustrating variations in multiple mental scales for "Horror (Concentration)" contents.

FIG. 19 is a table illustrating variations in multiple mental scales for "Horror (Notconcentration)" contents.

FIG. 20 is a table illustrating variations in subjective psychological indices for "positive" contents.

FIG. 21 is a table illustrating variations in subjective psychological indices for "Negative" contents.

FIG. 22 is a table illustrating variations in subjective psychological indices for "Horror (Concentration)" contents.

FIG. 23 is a table illustrating variations in subjective psychological indices for "Horror (Notconcentration)" contents.

FIG. 25 is a table illustrating evaluations of physiological indices for each content.

FIG. 30 is a table illustrating the structure of a neural network for use in estimation of "Excitement-Calm", "stress coping style", and "preference".

FIG. 32 is a table illustrating evaluation of subjective psychological indices for each content.

FIG. 33 is a table illustrating evaluation of psychological indices for each content.

FIG. 34 is a table illustrating a positive distinction rate of preference and a viewing mode for TV contents.

DESCRIPTION OF EMBODIMENT

One embodiment of the present invention is described below with reference to the attached drawings.

[Structure]

Figure 1:
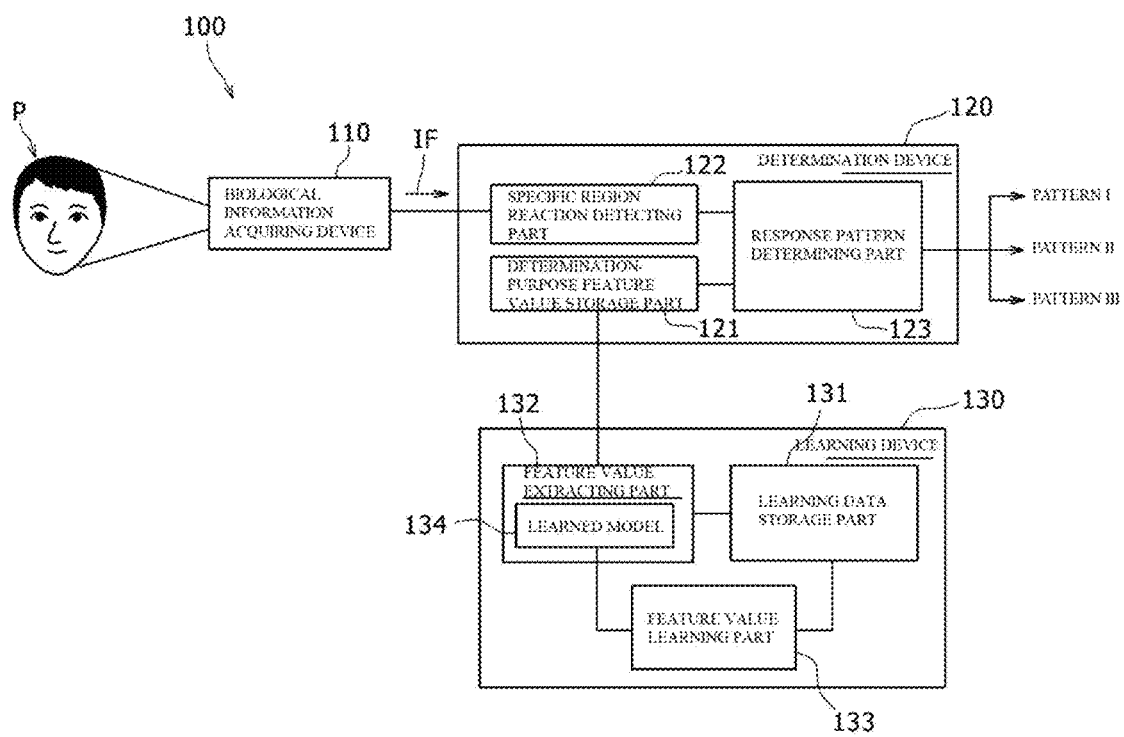
FIG. 1 is a block diagram of one embodiment of a stress coping style determination system according to the present invention.

A stress coping style determination system 100 of one embodiment illustrated in FIG. 1 has a biological information acquiring device (biological information acquiring part) 110, a determination device (determining part) 120, and a learning device (machine learning part) 130.

The biological information acquiring device 110 is a device to acquire biological information of a test subject P in a non-contact state.

As a most suitable example of biological information, a facial image IF can be taken. In the following description, a case is described in which the facial image IF is used as biological information.

The facial image IF may be a facial thermal image or a facial visible image. When the facial image IF is a facial thermal image, infrared thermography is used as the biological information acquiring device 110. When the facial image IF is a facial visible image, the biological information acquiring device 110, a so-called camera as a visible image taking device is used.

As described above, the "facial visible image" is a color image acquired by taking an image of the facial surface of a test subject with a camera widely used in general, that is, a device having an optical system for image formation to take an image. Also, the "facial thermal image" is an image acquired by analyzing infrared rays emitted from the facial surface of the test subject and presenting a thermal distribution as a drawing, and is acquired by taking an image with infrared thermography.

In this case, images taken by the camera are of visible light (wavelength of 380 nm to 800 nm). On the other hand, the thermal distribution image with infrared thermography is of infrared rays (wavelength of 800 nm or longer). Thus, only the difference between these cases resides simply in wavelength. Thus, infrared thermography and the general camera can both be used as the biological information acquiring device 110.

The determination device 120 is achieved by installing a program according to the present invention on a general-purpose computer and executing the program.

The determination device 120 is a device having a function of determining a stress coping style of the test subject based on the facial image IF acquired by the biological information acquiring device 110 and a response pattern specified in advance. The response pattern includes patterns of three types formed of "active coping" (Pattern I), "passive coping" (Pattern II), and "no coping" (Pattern III). The response pattern is specified by a hemodynamic parameter.

The hemodynamic parameter includes a plurality of parameters among a mean blood pressure (MBP), a heart rate (HR), a cardiac output (CO), a stroke volume (SV), and a total peripheral resistance (TPR).

The determination device 120 includes a determination-purpose feature value storage part 121, a specific region reaction detecting part 122, and a response pattern determining part 123.

The determination-purpose feature value storage part 121 is a functional block having stored therein a spatial feature value corresponding to "active coping", a spatial feature value corresponding to "passive coping", and a spatial feature value corresponding to "no coping". The spatial feature values stored in the determination-purpose feature value storage part 121 are spatial feature values extracted by the learning device 130. When the facial image IF is a facial thermal image, a facial skin temperature distribution can be taken as an example of the spatial feature value.

The specific region reaction detecting part 122 is a functional block which detects a stress response of an anatomical specific region of the facial surface of the test subject P included in the facial image IF. The anatomical specific region is one or a plurality of regions specified by an anatomical finding as a region with a relatively small individual difference. As an example of the anatomical specific region, a nose top can be taken.

The response pattern determining part 123 is a functional block which determines that the stress coping style of the test subject P is any response pattern among "active coping" (Pattern I), "passive coping" (Pattern II), and "no coping" (Pattern III), based on the stress response detected by the specific region reaction detecting part 122 and each spatial feature value stored in the determination-purpose feature value storage part 121.

The learning device 130 has a learning data storage part 131, a feature value extracting part 132, and a feature value learning part 133. The learning device 130 is achieved by installing a program according to the present invention on a general-purpose computer and executing the program.

Figure 2:
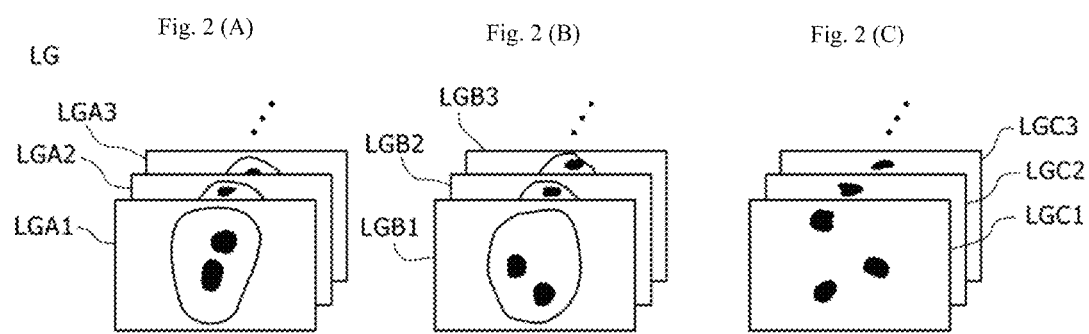
FIG. 2(A) is a descriptive diagram conceptually and exemplarily illustrating a learning-purpose facial image group provided with a label of "active coping".
FIG. 2(B) is a descriptive diagram conceptually and exemplarily illustrating a learning-purpose facial image group provided with a label of "passive coping".
FIG. 2(C) is a descriptive diagram conceptually and exemplarily illustrating a learning-purpose facial image group provided with a label of "no coping".

The learning data storage part 131 is a functional block having stored therein a plurality of learning-purpose facial images LG labelled so as to correspond to "active coping", "passive coping", and "no coping", respectively. In FIG. 2 the learning-purpose facial images LG are conceptually and exemplarily illustrated. LGA1, LGA2, LGA3, . . . illustrated in FIG. 2(A) are a learning-purpose facial image group provided with a label "active coping". LGB1, LGB2, LGB3, . . . illustrated in FIG. 2(B) are a learning-purpose facial image group provided with a label "passive coping". LGC1, LGC2, LGC3, . . . illustrated in FIG. 2(C) are a learning-purpose facial image group provided with a label "no coping".

The feature value extracting part 132 is a functional block which extracts the spatial feature value of the facial image from the learning-purpose facial images LG by using a learned model 134. The learned model 134 is generated by using the plurality of learning-purpose facial images LG labelled so as to correspond to the response patterns specified by the hemodynamic parameters as teacher data and machine-learning the spatial feature value of the facial image of the test subject P included in the learning-purpose facial images LG.

The feature value learning part 133 is a functional block which changes a network parameter of the learned model 134 so that extraction accuracy of the spatial feature value by the feature value extracting part 132 is enhanced, based on a relation between the extraction result by the feature value extracting part 132 and the label provided to the learning-purpose facial image LG as an extraction target.
[Operation]

Figure 3:
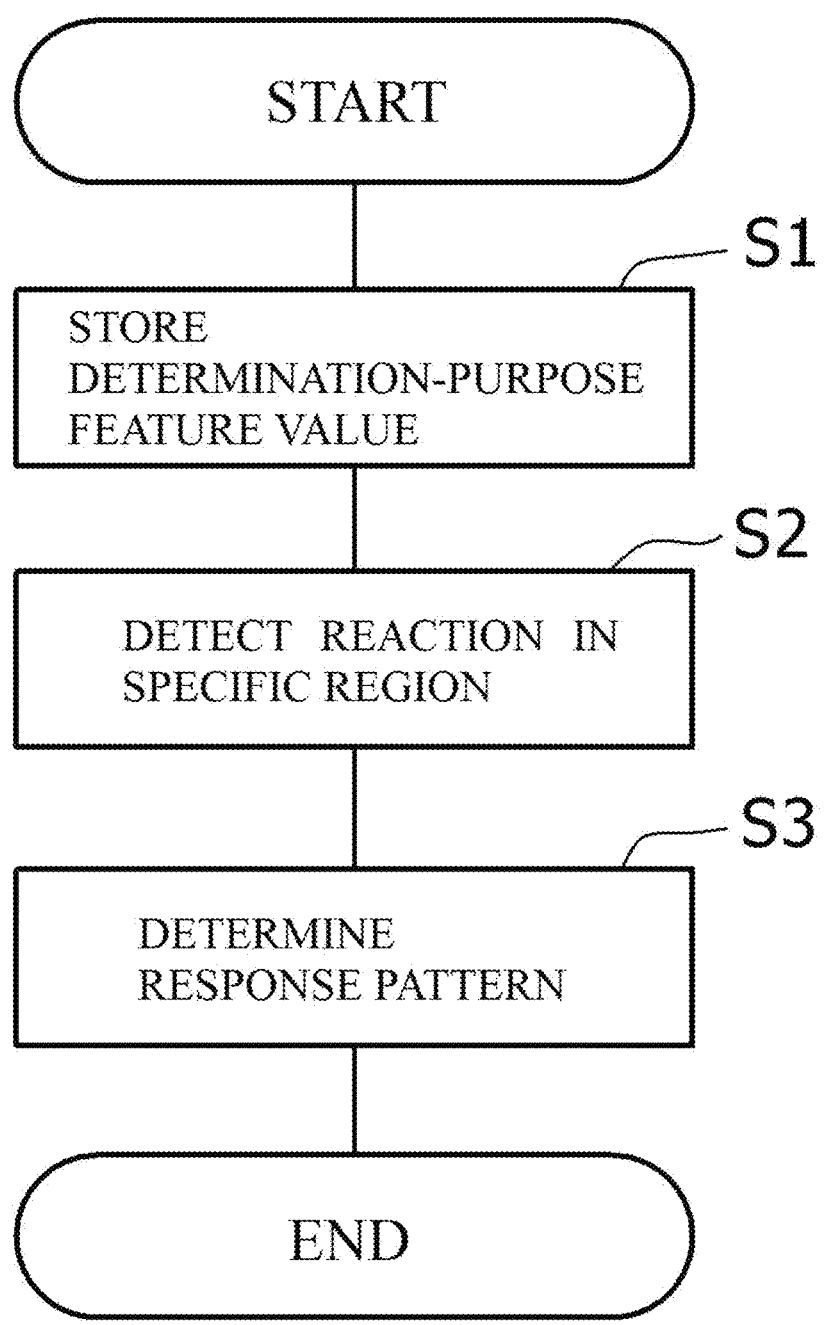
FIG. 3 is a flowchart illustrating process details of a determination device configuring the stress coping style determination system of FIG. 1.
Figure 4:
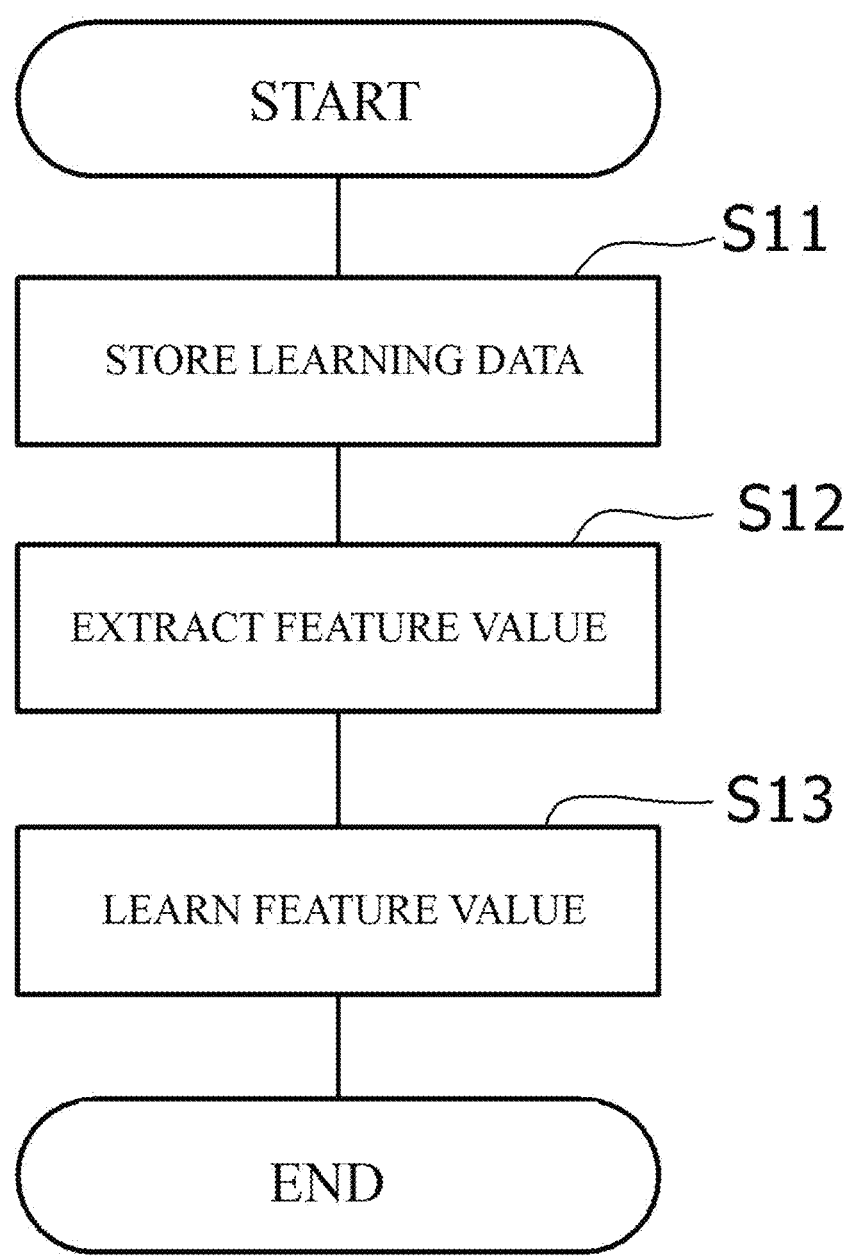
FIG. 4 is a flowchart illustrating process details of a learning device configuring the stress coping style determination system of FIG. 1.

Next, a flow of process in the determination device 120 and the learning device 130 in the stress coping style determination system 100 configured as described above is described by following flowcharts of FIG. 3 and FIG. 4.

The determination device 120 executes, as illustrated in FIG. 2, a determination-purpose feature value storing process S1, a specific region reaction detecting process S2, and a response pattern determining process S3.

The determination-purpose feature value storing process S1 is a process of storing the spatial feature values extracted by the learning device 130, that is, the spatial feature value corresponding to "active coping", the spatial feature value corresponding to "passive coping", and the spatial feature value corresponding to "no coping", in the determination-purpose feature value storage part 121.

The specific region reaction detecting process S2 is a process of detecting a stress response of the anatomical specific region of the facial surface of the test subject P included in the facial image IF taken by the biological information acquiring device 110.

The response pattern determining process S3 is a process of determining that the stress coping style of the test subject P is any response pattern among "active coping", "passive coping", and "no coping", based on the stress response detected by the specific region reaction detecting process S2 and each spatial feature value stored in the determination-purpose feature value storage part 121.

The learning device 130 executes, as illustrated in FIG. 4, a learning data storing process S11, a feature value extracting process S12, and a feature value learning process S13.

The learning data storing process S11 is a process of storing the plurality of learning-purpose facial images LG labelled so as to correspond to "active coping", "passive coping", and "no coping", respectively, in the learning data storage part 131.

The feature value extracting process S12 is a process of extracting the spatial feature value of the facial image of the test subject included in the learning-purpose facial image LG from the learning-purpose facial images LG by using the learned model 134.

The feature value learning process S13 is a process of changing a network parameter of the learned model 134 so that extraction accuracy of the feature value at the feature value extracting process S12 is enhanced, based on a relation between the extraction result at the feature value extracting process S12 and a label provided to the learning-purpose facial image LG as an extraction target.
[Spatial Feature Value]

In the present embodiment, as a spatial feature value, a fractal dimension calculated based on the facial image IF can be used. With the use of the fractal dimension, the spatial feature value can be easily and accurately converted into numbers.

Figure 39:
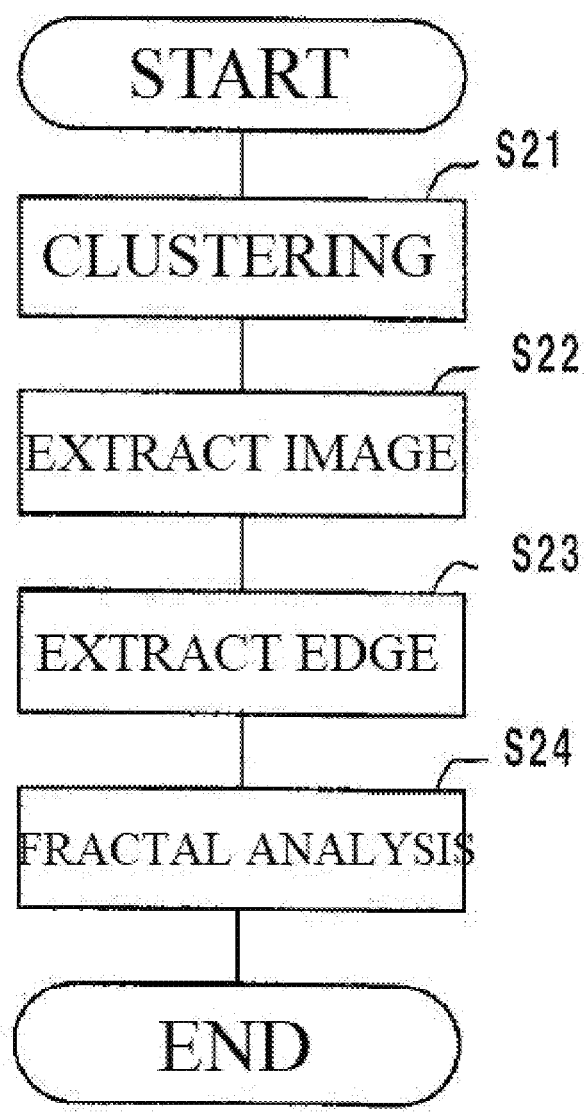
FIG. 39 is a flowchart exemplarily illustrating a method of finding a fractal dimension as a spatial feature value.

Any method of finding a fractal dimension as a spatial feature value can be taken. In a process flow exemplarily illustrated in FIG. 39, a fractal dimension is found by executing a series of processes formed of a clustering process S21, an image extracting process S22, an edge extracting process S23, and a fractal analysis process S24.

Figure 40:
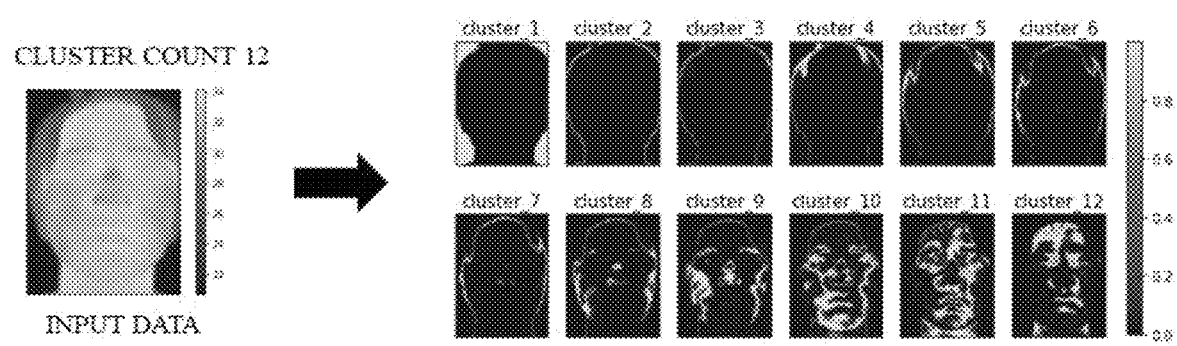
FIG. 40 is a descriptive diagram illustrating an embodiment of clustering process in FIG. 39.

The clustering process S21 is a process of subjecting the facial image IF to clustering with respect to a temperature distribution. Although any clustering scheme can be taken, as a scheme suitable for the present embodiment, the Fuzzy-c-means method can be taken. The Fuzzy-c-means method is a scheme in which, instead of thinking an either-or problem such as whether a data group belongs a cluster, it is assumed that, other than a situation in which data completely belongs to a single cluster (k-means method), data belongs to a plurality of clusters to some extent and the degree of belonging of data to each cluster (membership grade) is ambiguously represented. FIG. 40 illustrates an example in which the input image (facial image IF) is subjected to clustering by setting the number of cluster at 12. In the example of FIG. 40, cluster 1 belongs to the lowest temperature distribution, and cluster 12 belongs to the highest temperature distribution.

The image extracting process S22 is a process of extracting a cluster image in the temperature distribution in a temperature region at a predetermined temperature or higher from among the plurality of cluster images acquired at the clustering process S21. In an example of FIG. 41, among the images of cluster 1 to cluster 12 exemplarily illustrated in FIG. 40, cluster 8 to cluster 12 are extracted, which are images with membership grades including temperatures of a facial region.

Figure 41:
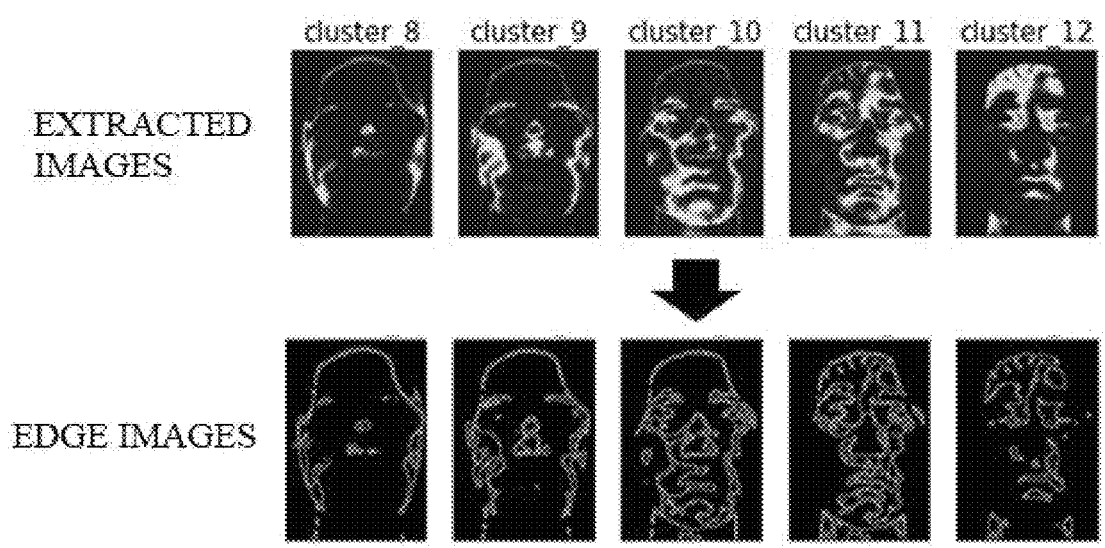
FIG. 41 is a descriptive diagram illustrating an embodiment of an image extraction process and an edge extraction process in FIG. 39.

The edge extracting process S23 is a process of detecting edge portions of the image extracted at the image extracting process S22 and generating an edge figure formed of line segments represented by the edge portions. Although any edge detection scheme can be taken, as a scheme suitable for the present embodiment, the Canny method can be taken. The Canny method is a scheme of detecting edges through a noise removal process by a Gaussian filter, an intensity gradient (edge) extraction process by a Sobel filter, a minimum cut-off suppression process of removing a portion other than a portion where the edge strength is maximum, and a hysteresis threshold process of determining whether the edge is true with a threshold using hysteresis. In the example of FIG. 41, edge portions of the images of cluster 8 to cluster 12 are detected by the Canny method, and edge figures formed of line segments represented by the edge portions are generated.

The fractal analysis process S24 is a process of finding a fractal dimension of the edge figure generated at the edge extraction process S23. The fractal dimension is an index quantitatively indicating self-similarity or complexity of figures and phenomena, and generally has a noninteger value. Although any fractal analysis scheme can be taken, as a scheme suitable for the present embodiment, the box counting method can be taken. The box counting method is a method of finding a fractal dimension from an absolute value of a slope of a straight line when the figure as an analysis target is divided into square boxes (in a grid) and a relation between the size of the box and the total number of boxes including the figure are subjected to linear approximation on a log-log graph.

The mathematical expression for a fractal dimension (D) is represented by the following equation. r is the size of the box, and N(r) is the number of boxes. [Equation 1]

$$D = -\lim_{r \to 0} \frac{\log N(r)}{\log r} \quad \text{[Equation 1]}$$

Figure 42:
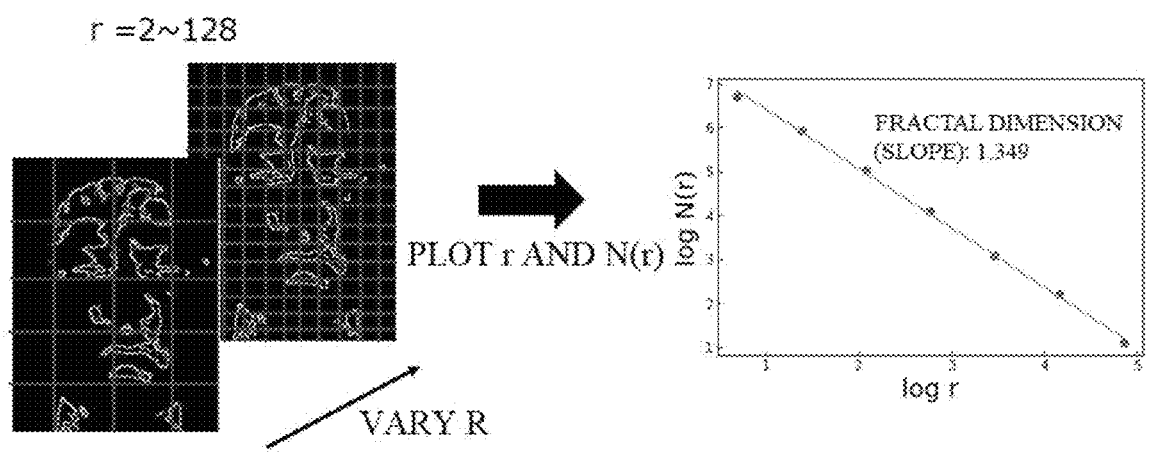
FIG. 42 is a descriptive diagram illustrating an embodiment of a fractal analysis process in FIG. 39.

FIG. 42 illustrates an example of calculation of a fractal dimension of an edge figure of cluster 12 in FIG. 41. In this example, as for the edge figure of cluster 12, by varying r in a range of 2 to 128 and plotting r and N(r) on a log-log graph, a value of 1.349 is obtained.

[Operation and Effects]

In the stress coping style determination system 100 configured as described above, the facial image IF of the test subject P is taken by the biological information acquiring device 110. The taken facial image IF is inputted to the determination device 120. Based on the input facial image IF and the response pattern (Pattern I, II, III) specified by the hemodynamic parameter, that is, any of the mean blood pressure, the heart rate, the cardiac output, the stroke volume, and the total peripheral resistance, the determination device 120 determines that the stress coping style of that test subject P is a style indicating any pattern among Patterns I, II, and III.

Therefore, according to this stress coping style determination system 100, the stress coping style of the test subject P can be determined in a non-contact state based on the facial image IF of the test subject P. Thus, it is possible to grasp the type of stress being felt by the test subject P without imposing constraints on the behavior of the test subject P.

Also, based on the reaction and response pattern (Pattern I, II, III) of the anatomical specific region of the facial surface included in the facial image IF of the test subject P, this stress coping style determination system 100 determines the stress coping style of that test subject P. The anatomical specific region is one or a plurality of regions specified by an anatomical finding as a region with a relatively small individual difference.

Therefore, according to this stress coping style determination system 100, a general-purpose system for stress coping style determination can be constructed.

Also, in this stress coping style determination system 100, the feature value corresponding to "active coping", the feature value corresponding to "passive coping", and the feature value corresponding to "no coping" are extracted by the learning device 130. The learning device 130 has stored therein the plurality of learning-purpose facial images LG labelled so as to correspond to "active coping", "passive coping", and "no coping", respectively, extracts the spatial feature value of the facial image from these learning-purpose facial images LG by using the learned model 134, and changes the network parameter of the learned model LG so that extraction accuracy of the spatial feature value of the facial image is enhanced, based on the relation between that extraction result and the label provided to the learning-purpose facial image LG as an extraction target. As learning of the learned model LG advances, extraction accuracy of the spatial feature value of the facial image improves, and accuracy of the spatial feature values stored in the determination-purpose feature value storage part 121 also improves.

Therefore, according to this stress coping style determination system 100, as learning of the learned model LG in the learning device 130 advances, determination accuracy of the stress coping style can be improved.

Also, according to this stress coping style determination system, the spatial feature value is converted into numbers by a fractal dimension, it is possible to more improve determination accuracy of the stress coping style.

Note that the present invention is not limited to the above-described embodiment. For example, while the stress coping style determination system 100 includes the learning device 130 in the above-described embodiment, the learning device 130 can be omitted. When the learning device 130 is omitted, the spatial feature values extracted or generated by means other than the learning device 130 are stored in the determination-purpose feature value storage part 121 of the determination device 120.

<Experiment Example 1>

Described below is one experiment example for collecting feature value data stored in the determination-purpose feature value storage part 121 according to the present embodiment.

1. Experiment Method

Figure 6:
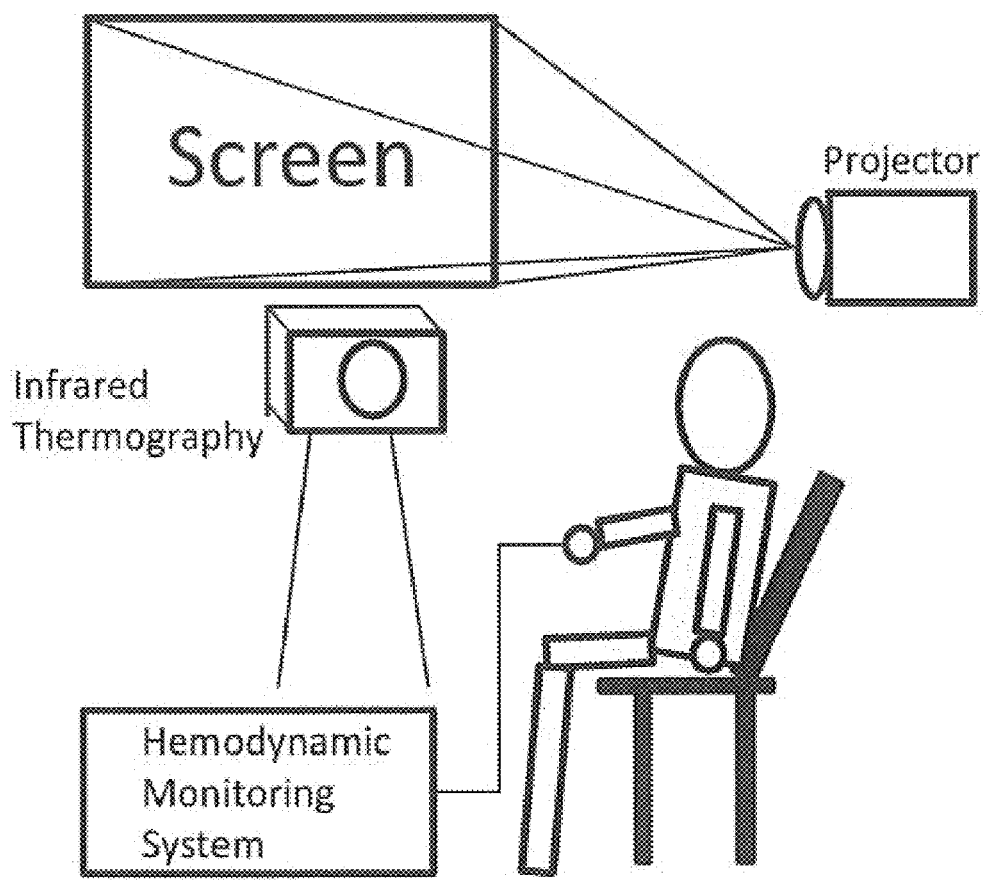
FIG. 6 is a conceptual diagram illustrating a measurement system.

The experiment was performed in a shielded room at $25.0 \pm 1.5°$ C. with eight healthy adult males at ages 18 to 21. A measurement system is illustrated in FIG. 6. Each test subject was seated, and had a measurement cuff of a continuous blood-pressure-hemodynamics measuring instrument (Finometer model 2, manufactured by Finapres Medical Systems B. V.) attached to the second joint of the middle finger of the left hand.

As hemodynamic parameters, a mean blood pressure (MBP), a heart rate (HR), a cardiac output (CO), and a total peripheral resistance (TPR) were measured. To measure a facial thermal image, infrared thermography (TVS-200EX, AVIONICS) was set at a position 1.2 m ahead at an angle of view allowing measurement of the entire facial surface, and the image-taking interval is set at 1 fps. For measurement of a facial skin temperature, the test subject was seated in a chair with a backrest, and a screen of a computer was projected by a projector toward a wall at a distance of 1.55 m.

Figure 7:
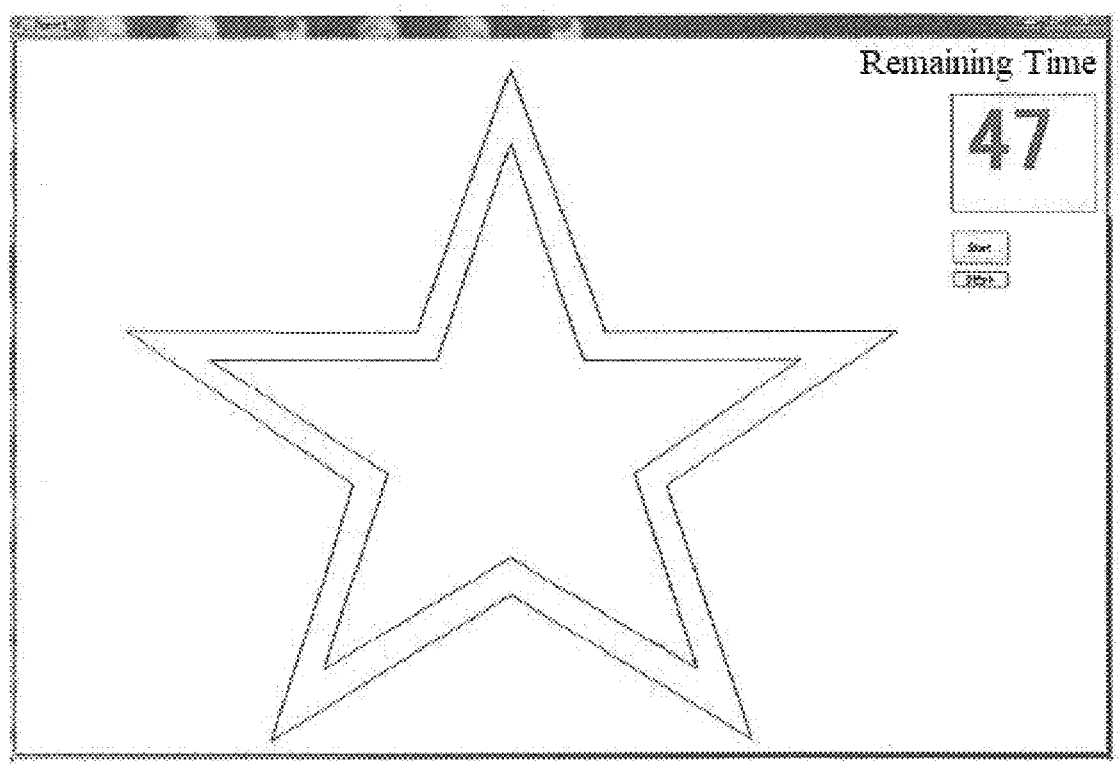
FIG. 7 is a conceptual diagram illustrating a mirror drawing test.

The experiment is configured of pre-task resting closed eyes 60 s (Rest 1), active problem 60 s (Task 1), and no-coping problem 60 s (Task 2), passive problem 60 s (Task 3), and post-task resting closed eyes 60 s (Rest 2). A mental arithmetic problem was solved in the active problem, a mirror drawing problem was solved in the passive problem, and resting closed eyes was performed in the no-coping problem. In the mental arithmetic problem, a two-digit addition for every four seconds was performed on the screen of a computer. Each test subject was not notified about whether the answer of the mental arithmetic was correct on each occasion. Also, in the mirror drawing problem, the test subject was taught to draw a line passing between lines of a star-shaped figure (refer to FIG. 7) reproduced on the computer and displayed on the screen by using a mouse with the right hand. The movement of the mouse and the movement of a cursor on the screen were reversed in vertical and horizontal directions.

On the star-shaped figure, a cursor and a cursor path were displayed. When the cursor went off the path, the cursor was returned to the initial position and the entire path was erased. A circling start position was set at the uppermost part of the star shape. As a no-coping problem, resting closed eyes were used. By taking an average value of Rest 1 in the hemodynamic parameters as a baseline, a subtraction was performed for normalization.

2. Analysis Method 2-1 Determination of Hemodynamic Parameter

Figure 8:
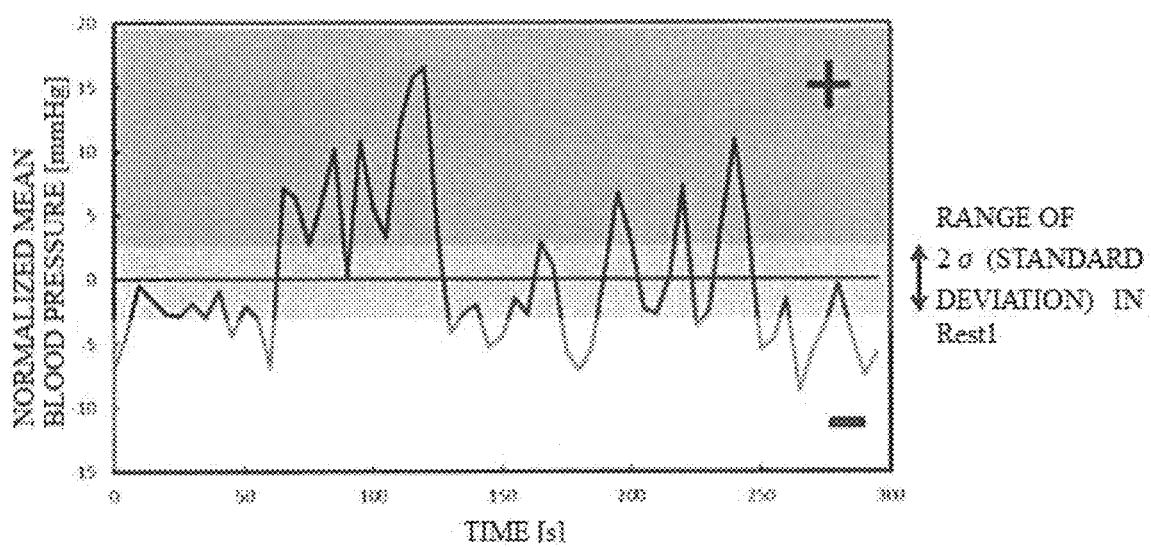
FIG. 8 is a graph illustrating changes with time of MBP (mean blood pressure).

FIG. 8 illustrates time-series changes in normalized MBP of test subject A. As for each hemodynamic parameter, a range of values equal to or larger than baseline+$2\sigma$ ($\sigma$: standard deviation of the hemodynamic parameter in Rest 1) was defined as "+" and a range of values equal to or smaller than base line−$2\sigma$ was defined as "−". Based on the pattern reactions in Table 1, the hemodynamic parameters were determined as "Pattern I" (active coping), "Pattern II" (passive coping), and "No coping" when the parameter is not relevant to either of them. Also, thermal images taken among Task 1 to Task 3 were labelled based on the determination as to the hemodynamic parameter.

2-2 Generation of Input Data

For the purpose of using the labelled thermal images for machine learning, a facial surface portion was trimmed to 151×171 pixels for grayscale processing, thereby creating facial thermal images. Also, to match the number of labelled facial thermal images (input data) with each stress coping, random cropping, addition of white Gaussian noise, and contrast adjustment were performed for data expansion.

2-3 Machine Learning by Using CNN

In this experiment, by using a convolutional neural network (CNN), personal determination models of stress coping styles were constructed based on the facial skin temperature distribution, and feature values associated with stress coping style were extracted.

Figure 9:
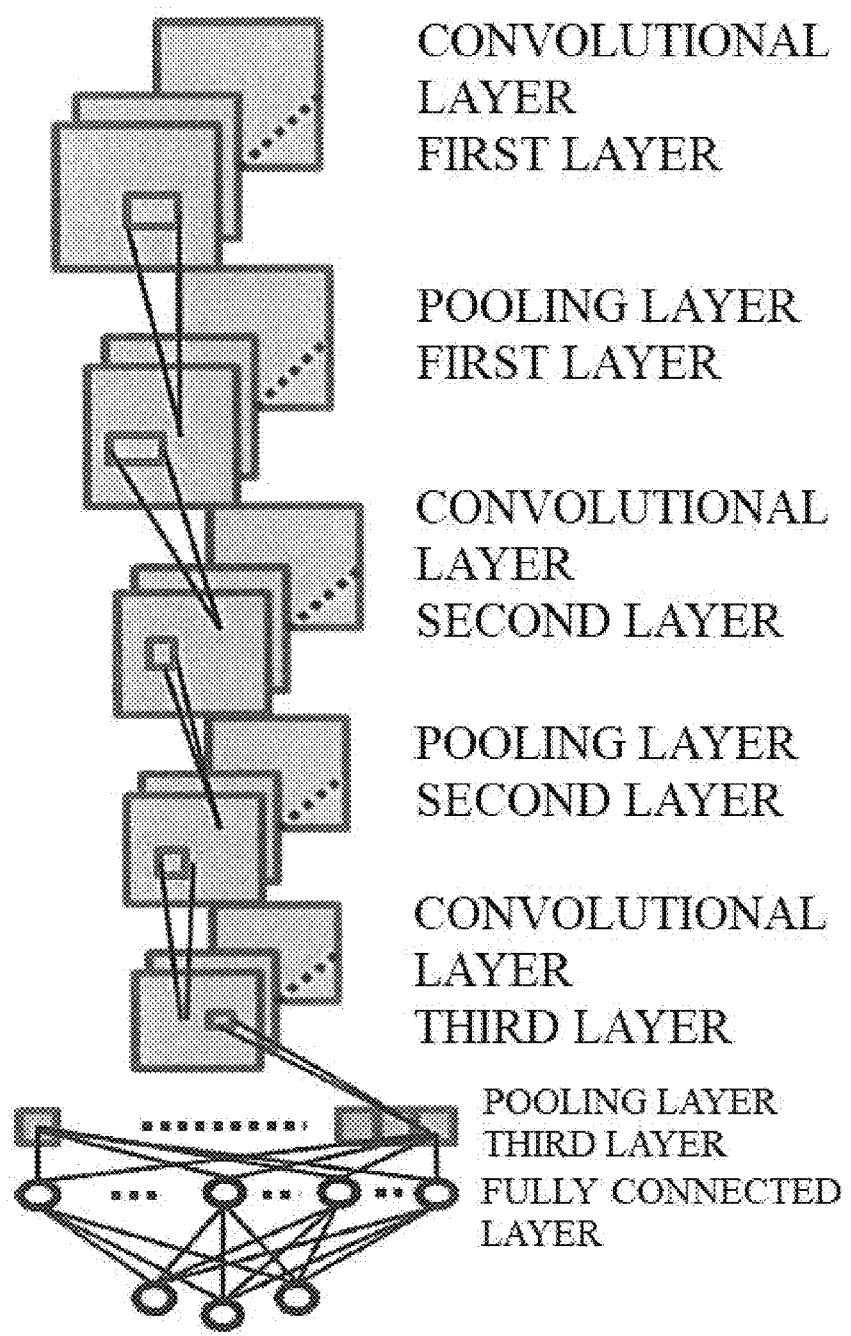
FIG. 9 is a schematic diagram illustrating a CNN (convolutional neural network).

The structure of the CNN is formed of three convolutional layers for extracting a feature value, three pooling layers, and one fully connected layer for making a determination. The structure of the CNN is illustrated in FIG. 9, and parameters of filters of the convolutional layers and the pooling layers are illustrated in FIG. 10 and FIG. 11. Feature analysis associated with the stress coping styles was performed based on a feature map representing weighting of the convolutional layers of the CNN.

3. Results and Discussion

A feature map of the second convolutional layer when a facial thermal image of each stress coping style is inputted to the CNN is illustrated in FIG. 12 for each test subject.

As a result of observing the feature map for each coping style among the test subjects, it was indicated that a feature region presented in each stress coping style varies, for example, in particular, in test subject B, a feature was observed on the left cheek at the time of active coping and no stress coping and on the right cheek at the time of passive coping. As a result of viewing the feature map of each test subject, a feature was presented at a nose part in most test subjects, but an individual difference was observed in the feature presenting regions for each test subject.

As a factor for the individual difference observed in the feature presenting regions for each test subject, a difference in the structure of the vessels and fat can be thought. However, by specifying an anatomically meaningful feature region, it can be thought to lay out a road map to construction of a general model for stress coping determination.

4. Summary

In this experiment, by using the CNN, determination of a stress coping style based on the facial skin temperature distribution and extraction of a feature related to the stress coping style were tried. As a result, the feature distribution presented in the facial skin temperature distribution changes depending on the stress coping style and, furthermore, an individual difference among individuals was observed in the feature distribution associated with the stress coping style.

REFERENCE DOCUMENTS

[1] Yukihiro Sawada: "New Physiopsychology" (under editorship of Yo Miyata), Chapter 10, Kitaohji Shobo Co., Ltd., pp. 172-195 (1998)
[2] Yuichiro Nagano: Cardiovascular Responses During a Competitive Mirror Drawing Task, Journal of Physiological Psychology and Psychophysiology, 22 (3): pp. 237-246 (2004)
[3] Shizuka Bando, Hirotoshi Asano, Akio Nozawa: "Analysis of Physiological effects regarding display media for book reading", IEEJ Transactions on Electronics, Information and Systems Vol. 135, No. 5, pp. 520-525 (2015)
[4] Takuya Watanuki, Akio Nozawa: "Analysis of the Mode of Viewing TV Based on the Stress Coping Style", IEEJ Transactions on Electronics, Information and Systems Vol. 134, No. 2, pp. 205-211 (2014)
[5] Kyu Hioki, Akio Nozawa, Tota Mizuno, Hideo Ide: "Physiological Evaluation of Mental Workload in Time Pressure", IEEJ Transactions on Electronics, Information and Systems, Vol. 127, No. 7, pp. 1000-1006 (2007)
[6] Hiroki Ito, Shizuka Bando, Kosuke Oiwa, Akio Nozawa: "Evaluation of Variations in Autonomic Nervous System's Activity During the Day Based on Facial Thermal Images Using Independent Component Analysis", IEEJ Transactions on Electronics, Information and Systems, Vol. 138, No. 7, pp. 1-10, (2018)
[7] Kenta Matsumura, Yukihiro Sawada: "Cardiovascular Responses During Two Kinds of Mental Arithmetic Tasks", The Japanese Journal of Psychology, Vo. 79, No. 6, pp. 473-480 (2008)

Also, two examples of experiments and studies by the inventors of the present application serving as basic studies for the stress coping style determination system according to the present invention are described below as application examples (embodiments) of the present invention.

Unlike the present invention in which "biological information of a test subject is acquired in a non-contact state", these examples of experiments were performed by using a continuous blood-pressure meter and attaching a cuff to a test subject. However, similarly to the present invention, the physiological/psychological states of viewers when viewing video contents based on a hemodynamic parameter were analyzed, classified and evaluated. Therefore, the present invention can be applied to, for example, determination as to the stress style of the test subject in the situation as described above.

<Experiment Example 2>

Gist of Experiment

Today, we are surrounded by many pieces of information equipment. Of these, television, since its invention, has been set in a living room at home or the like and has been recognized as the centerpiece of news media and entertainment media. However, with widespread of small-sized and sophisticated information communication equipment due to the recent advance of IT technologies and with development of information network environments, the way the information media should be has been greatly transformed. In recent years, the television viewing mode has also been greatly transformed.

Nishigaki states that viewers are entirely far away from "concentrating viewers" because they are doing chores or operating portable phones while turning the television switch always ON[1]. However, if those transformed viewing modes can be grasped, a new additional value can be provided to television, such as adjusting the mood, feeling, and action to a desired direction by design of TV contents.

Fujiwara and Saito conducted an opinion poll, and Ohno conducted a questionnaire survey, and they listed, as the reasons for viewing television, "to kill time", "to enjoy funny programs", "for cultural enrichment and knowledge acquirement", "as a habit for no particular purpose", "to escape from burdensome real life", "for refreshment", "BGM", "for family togetherness", so forth[2][3].

Also, Takahashi et al. classify times for viewing television as "when having breakfast", "when commuting to office", "during household chores", "when relaxing weekdays at home", and so forth[4]. Furthermore, Tomomune et al. classify television viewing modes as "dedicated viewing" in a state in which "the body and the mind and body are concentrating on television", "doing-another-thing & dedicated switching viewing" in a state of "viewing a desired program as doing another thing", "making-time-comfortable viewing" in a state in which "the body is concentrating on television although there is no particular program desired to be viewed", and so forth[5].

As described above, it has been revealed that the viewing mode is varied and is transformed due to factors such as time, venue, feeling, and so forth. Preference in TV video may also be one factor for transforming the viewing mode. However, there is no study of classifying viewing modes based on preference. Moreover, most studies of determining these viewing modes use an opinion poll or a psychological response such as post introspective evaluation, and no study of classifying viewing modes by using a physical response.

Since video and audio of television are audiovisual stimulations of the living body, they themselves are regarded as stressors. A stressor promotes the living body to perform stress coping, and brings a physiological/psychological change as a stress response. When various television contents are regarded as stressors, their physiological stress response is expected to vary depending on coping with the contents, that is, the viewing mode. Nomura et al. classify coping modes with e-learning contents based on a cardiovascular-system index[6].

Thus, in this study, for the purpose of analyzing a viewing mode for television contents based on a cardiovascular-system index, the cardiovascular system was measured by a continuous blood-pressure meter, the facial skin was measured in a non-contact state by an infrared thermography device, and an electrocardiogram and an electroencephalogram were taken by a digital biological amplifier, thereby evaluating activation of the central nervous system and activation of the autonomic nervous system. In particular, the viewing mode at the time of viewing TV video was analyzed based on the stress coping style using a hemodynamic parameter and preference in TV video.

2. Factor Extraction Experiment

The viewing mode was thought to be influenced by video contents and personal preference for them, and factor classification is performed with a preliminary experiment.

<2-1> Experiment Conditions Test subjects are twenty healthy students enrolled in universities (ages: 19-22; average age: 21.1; eleven males; and nine females). To the test subjects, the details, purpose, and investigation target of the experiment were sufficiently described in advance orally and in writing, and a consent to cooperate the experiment was confirmed with his/her signature. Measurement were performed in a shielded room at a room temperature of 26.0±1.6° C. without convection, and no temperature input from outside was present.

Each test subject is seated and views video contents of ten types (news, sports, documentary, music, horror, variety, drama, animation, cooking, and shopping) for five minutes by using a liquid-crystal television (55 inches, HX850, BRAVIA, manufactured by SONY) set at a position 2 m ahead. The video contents were reproduced by a DVD player (SCPH-3900, manufactured by SONY). The video contents to be viewed are not published until the test subject views. Also, to remove the order effect, the order of video contents to be viewed is set as random.

<2.2> Experiment Procedure As illustrated in FIG. 13, this experiment is configured of five-minute video viewing and one-minute resting-closed-eyes states R1 and R2 before and after viewing. Also, preference and a sense of immersion in each of the video contents were evaluated by Visual Analogue Scale (hereinafter abbreviated as VAS) and a sense-of-immersion survey.

<2.3> Evaluation Method At the end of the experiment, intensity of subjective sense of "preference" was measured by using VAS. By arranging paired adjectives on both ends of a line segment and prompting the test subject to check any position on the line segment, psychophysical quantity of the test subject can be measured. As for words arranged on both ends of the scale, "really hate" to "really like" were taken. In addition, the sense of immersion in video was measured with a five-point scale (1: cannot be immersed at all-5: considerably immersed).

<2-4> Results and Discussion of Factor Extraction Experiment

Figure 14:
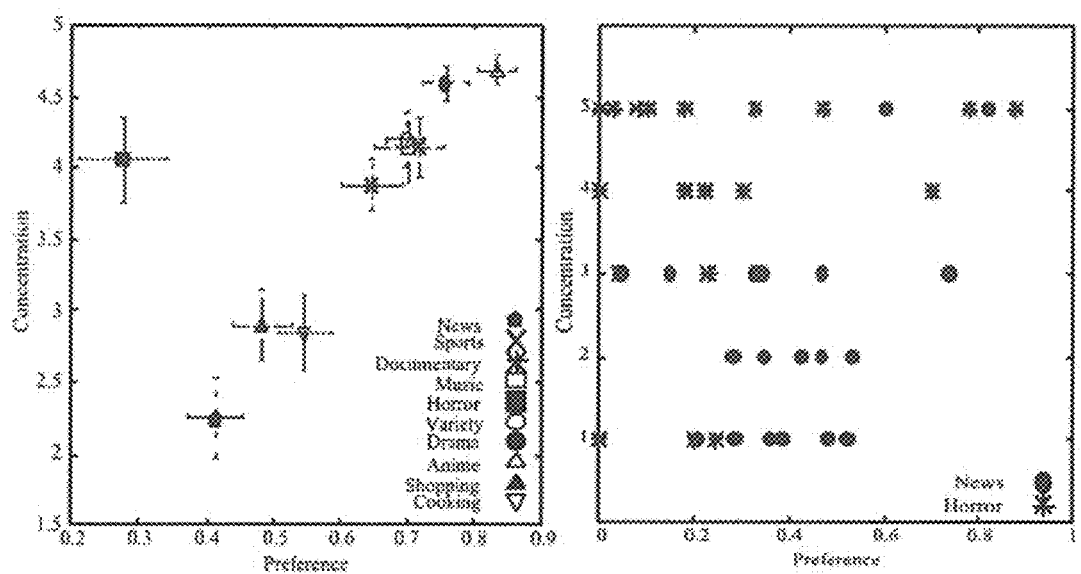
FIG. 14 is a graph illustrating a relation between preference and concentration.

On the left in FIG. 14, averages of all test subjects in preference and sense of immersion for contents of ten types are illustrated. Error bars in the drawing each represent a standard deviation of preference and sense of immersion. On the right in FIG. 14, preference and sense of immersion of twenty test subjects for news and horror are illustrated, which particularly have a large individual difference. When preference and the sense of immersion for each of the contents are viewed from the left in FIG. 14, average preference and sense of immersion have a proportional relation. In FIG. 14, N=20.

As for horror, a specific result was presented in which preference is low but the sense of immersion is high. The reason for this is thought to be so-called "curiosity of fear", in which horror is hated but is desired to be viewed all the more from curiosity. From the right in FIG. 14, since preference and the sense of immersion vary for each test subject, it can be found that an individual difference is large. That is, in the physiological measurement experiment, based on the above-described factor classification experiment, video contents with high immersion and positive preference (high preference), video contents with low immersion and negative preference (low preference), and horror video indicating a specific result with low preference but high immersion or low sense of immersion were presented to each test subject.

3. Physiological Measurement Experiment

Based on the factor extracted by the factor extraction experiment, physiological measurements were performed on the same test subjects again by using other video.

<3.1> Experiment Conditions Test subjects are fourteen healthy students (ages: 19-22; average age: 21.4; seven males; and seven females) enrolled in Japanese universities. In a shielded room similar to that in 2.1, an experiment was performed. To switch video contents and check a physiological measurement situation, one person performing the experiment attended in the same room. To acclimate the body surface temperature to the room temperature, the experiment was performed after the lapse of twenty minutes or more from the entry of the test subject into the room. Video contents with positive preference and negative preference were set for each test subject based on the results of the factor extraction experiment. Video contents with the highest preference among those with sense of immersion being 4 or higher and preference being 0.6 or higher were set as positive preference (hereinafter abbreviated as "Positive"), and video contents with the lowest preference among those with sense of immersion being 2 or lower and preference being 0.4 or lower were set as negative preference (hereinafter abbreviated as "Negative"). Thus, the video contents to be viewed are of three types: "Positive", "Negative", and "Horror".

<3.2> Experiment Procedure As with the factor extraction experiment, the procedure is configured of FIG. 13. Also, with VAS, Multiple mood scale (hereinafter abbreviated as MMS), and a survey of the sense of immersion, sensibility fluctuations and preference and the sense of immersion were evaluated with respect to each of the video contents.

Figure 15:
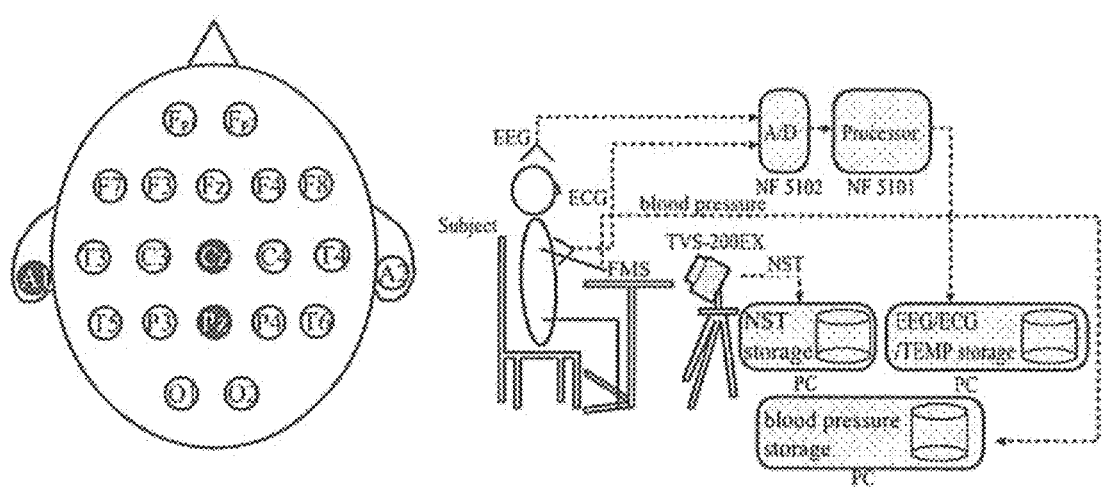
FIG. 15 is a diagram illustrating a state of brain wave electrode arrangement to the test subject and a measurement system.

<3.3> Measurement System The arrangement of a measurement system and an EEG measurement electrode is illustrated in FIG. 15. Each test subject was seated, and had a continuous blood-pressure meter, an electrode for EEG derivation, and an electrode for ECG derivation attached. As for the continuous blood-pressure meter (Finometer model 2, manufactured by Finapres Medical Systems B.V.), its cuff was attached to the second joint of the middle finger of the left arm, and recordings were made on a PC at a sampling frequency of 200 Hz. An infrared thermography device (TVS-200X) was set at a position 0.7 m ahead of the test subject at an angle allowing the face surface to be measured. Skin emissivity was set at 8-0.98, temperature resolution was set at $0.1°$ C. or lower, and recordings were made on the PC at a sampling frequency of 1 Hz. EEG was measured by the reference electrode method with the left ear (A1) as a reference. The position of the electrode for EEG derivation was set at one point (Pz) based on the international 10-20 method, and the electrode contact resistance was set at 10 kΩ or lower.

In general, the a wave is recorded at O1 and O2. However, in this study, attention was paid to the a wave power as a steady-state index of cerebrum activities, and calculation of its attenuation ratio is the only purposes. Thus, by focusing on convenience of attachment of the electrodes and a reduction in measurement stress on the test subject instead of a lateral difference or locality, near Pz was measured. In order to minimize inclusion of a myoelectrical potential, by following the NASA induction method, the electrode for ECG measurement was attached to an upper green part of the sternum (+) and the apex part (−). The ground electrode was at the parietal part (Cz) in common between EEG and ECG. An EEG signal and an ECG signal were amplified at a digital biological amplifier (5102, manufactured by NF ELECTRONIC INSTRUMENTS), and recorded via a processor box (5101, manufactured by NF ELECTRONIC INSTRUMENTS) on the PC at a sampling frequency of 200 Hz.

<3-4> Evaluation Method

In this study, correlations between physiological indices and psychological indices were analyzed. The physiological indices were a mean blood pressure (hereinafter abbreviated as MP), a heart rate (hereinafter abbreviated as HR), a stroke volume (hereinafter abbreviated as SV), a cardiac output (hereinafter abbreviated as CO), a total peripheral resistance (hereinafter abbreviated as TPR), and nasal skin temperature (hereinafter abbreviated as NST), electrocardiograms (hereinafter abbreviated as ECG), and electroencephalograms (hereinafter abbreviated as EEG). Frequency components of EEG from 8 Hz to 13 Hz are referred to as a wave, are presented conspicuously at the time of resting, closed eyes, and awakening, and are known to be attenuated when any condition is impaired[8]. In this study, for an EEG time series sampled at 200 Hz, Fourier transform (FFT) was performed on 1024 sample points for every ten seconds to find an a-wave power spectrum for every ten seconds. Furthermore, average a wave power was calculated in each of an R1 section and an R2 section of FIG. 13, a ratio of average a power in the R2 section with reference to the average a wave power in the R1 section was taken as an index for fluctuations in the degree of awakening before and after television viewing.

NST is known as an index of activity of the sympathetic nervous system governing the blood flow of the peripheral part. Since promotion and suppression of the sympathetic nervous system and temporal variations of NST are correlated well, in this study, the fluctuation amounts of NST for every ten seconds was used as a quantitative index for performance of activity of the sympathetic nervous system regarding video viewing. A positive value indicates suppression of activity of the sympathetic nervous system, and a negative value indicates promotion of activity of the sympathetic nervous system. In each measured increase of a thermal image time series of the nose part, a spatial average temperature in 10×10 pixels of the nose part was found and taken as an NST time series. HF is high frequency components of 0.15 Hz to 0.4 Hz of a heart beat variability spectrum, which are known as respiratory arrhythmia components[7].

HF is taken as an index of activity of the parasympathetic nerve system, and increases and decreases in accordance with promotion and suppression of the parasympathetic nerve system. From the ECG samples, an R-wave peak interval time series is found by threshold process and, after cubic spline interpolation, resampling is performed at 20 Hz. FFT process is performed on the resampled data for every 1 s to acquire a heart beat variability power spectrum time series. The number of pieces of data for FFT process was 512. In the time-series heart beat variability power spectrum, integration values in 0.15 Hz to 0.4 Hz bands were found and taken as an HF time series. It has been known that the hemodynamic parameter (MP, HR, SV, CO, TPR) presents a characteristic reaction pattern (Pattern I, Pattern II) in accordance with external stress, which is an important concept in understanding a physiological reaction of the cardiovascular system against stress.

Specifically, Pattern I is characterized in promotion of myocardial contraction activity and an increase in blood volume to the skeletal muscle due to vasodilation. This can be said as energy-consumption-type reaction (active coping), so to speak. On the other hand, Pattern II is characterized in peripheral vascular contraction, and also the heart rate generally decreases. This can be said as energy-saving-type reaction (passive coping)[7].

Also, as psychological indices, multiple mode scale MMS and VAS were taken. In MMS, temporary feelings and emotion states fluctuating depending on the condition where a target is placed were indexed with the multiple mode scale of eight types formed of depression-anxiety (hereinafter abbreviated as D-A), hostility (hereinafter abbreviated as H), fatigue (hereinafter abbreviated as F), activated (hereinafter abbreviated as A), inactivated (hereinafter abbreviated as I), affinity (hereinafter abbreviated as AF), concentration (hereinafter abbreviated as D), and startle (hereinafter abbreviated as S)[9]. Before the start and at the end of the experiment, intensities of subjective sense of four types, that is, "sense of awakening", "comfort/discomfort", "tired feeling", "preference", were measured by using VAS.

"Comfort/discomfort" and "sense of awakening" were selected as items for psychological evaluation in this study as basic components of Russell's emotion dualism[10]. In VAS, by arranging paired adjectives on both ends of a line segment and prompting the test subject to check any position on the line segment, psychophysical quantity of the test subject can be measured. As for words arranged on both ends of the scale, "very sleepy" to "clearly awaken" for the sense of awakening, "very discomfortable" to "very comfortable" for comfort/discomfort, and "very tired" to "very vigorous" for the degree of vigorousness, and "really hate" to "really like" for preference were taken. Each VAS was prepared on an independent paper sheet, and the test subject was taught to sequentially record in his/her own handwriting without recursive referencing. Furthermore, after the end of the experiment, the sense of immersion to video was measured with 5-point scale (1: not immersed at all to 5: considerably immersed). Note that, as a statistical analysis method, the paired t-test was used for a test of a difference before and after video viewing of each psychological index, and the Wilcoxon signed-rank test was used for the change amount in the entire TEST section of each physiological index.

<3.5> Results and Discussion Statistical analysis is performed on the psychological indices, and psychological responses at the time of TV video viewing and before and after TV video viewing are discussed. Note that since preference for horror video stimulation of all test subjects is 0.4 or less, attention is paid only to the sense of immersion. In evaluation of the sense of immersion in five stages after horror video viewing, 4 or 5 was classified as Horror (Concentration) (hereinafter abbreviated as "Horror (C)") and 1 or 2 as Horror (NotConcentration) (hereinafter abbreviated as "Horror (N)"). The results hereinafter are represented by classification of "Positive", "Negative", "Horror (C)", and "Horror (N)". The number of persons with "Horror (C)" is ten, and the number of persons with "Horror (N)" is four. Averages of the respective mood scales of MMS for all test subjects are illustrated in FIG. 16 to FIG. 19.

N=14 in FIG. 16, N=14 in FIG. 17, N=10 in FIGS. 18, and N=4 in FIG. 19. Averages of all test subjects in "comfort/discomfort", "sense of awakening", "vitality", "preference" and "sense of immersion" of the sense of immersion are illustrated in FIG. 20 to FIG. 23. N=14 in FIG. 20, N=14 in FIG. 21, N=10 in FIGS. 22, and N=4 in FIG. 23.

From FIG. 16, "Positive" significantly increased in A and AF and significantly decreased in F. On the other hand, from FIG. 17, "Negative" significantly increased in H and F. This is consistent with the act of viewing video contents with positive preference and negative preference. In FIG. 18, "Horror (C)" significantly decreased in A and I, and it can be presumed that displeasing emotions were aroused on the whole. Also, there are more scales with a significant difference in FIG. 18 than those in FIG. 19.

From these, in horror, it can be assumed that changes in emotion are larger in the case of immersion compared with the case of non-immersion. From FIG. 20, "Positive" significantly increased in comfort/discomfort, sense of awakening, and vitality. From these, it can be thought that video contents with positive preference brought positive comfort with "sense of exhilaration" and "comfort" to the test subjects.

By contrast, from FIG. 21, "Negative" significantly decreases in comfort/discomfort, sense of awakening, and vitality. Thus, it can be thought that video contents with negative preference brought negative discomfort with "depression" and "discomfort" to the test subjects. Also, from FIG. 22, "Horror (C)" significantly increases in sense of awakening and significantly decreases in comfort/discomfort and vitality. Thus, it can be thought that positive discomfort with "sense of awakening" and "discomfort"

Figure 24:
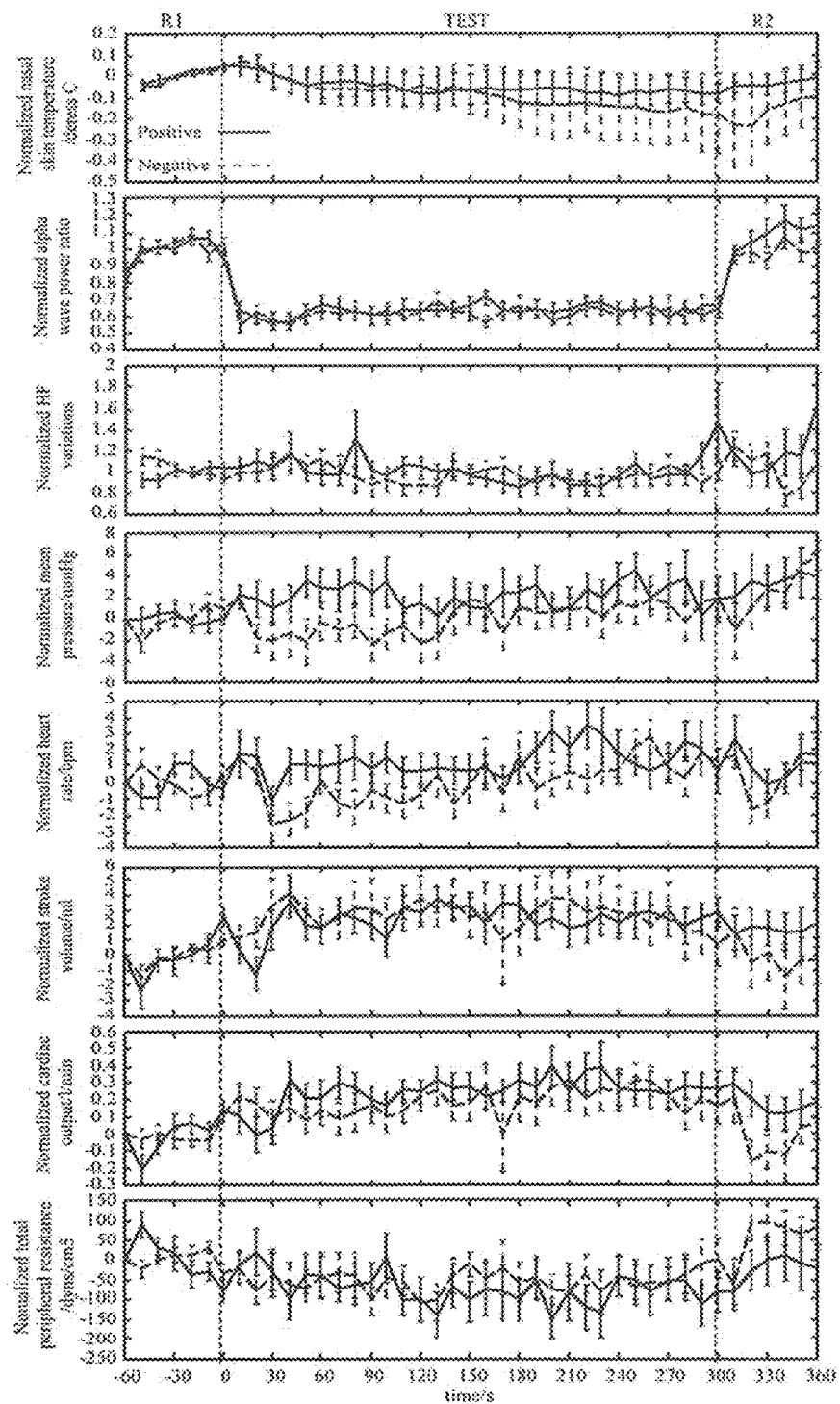
FIG. 24 is a table illustrating time-series variations of physiological indices for "Positive" and "Negative" contents viewing.

Next, physiological responses at the time of TV video viewing and before and after TV video viewing are discussed. Temporal variations of averages of physiological indices among the test subjects are illustrated in FIG. 24. In FIG. 24, N=14. From an upper stage, NST, a wave, HF, MP, HR, SV, CO, and TPR are illustrated. The start of the TEST section is set at 0. Each error bar in the drawing represents a standard error for each 10 s. Also, the baseline of the R1 section is set at 0 in NST, MP, HR, SV, CO, TPR, and the sense of immersion, and the baseline of the R1 section is set at 1 in the a wave and HF for normalization, and significance probability p of the Wilcoxon signed-rank test regarding deviation from the baseline in the entire TEST section is illustrated in FIG. 25 (+: $p<0.1$; *: $p<0.05$; **: $p<0.01$). In the table, P refers to a positive response and N refers to a negative response to each index. In FIG. 25, N=14.

From FIG. 24, when time-series changes for each index are viewed, "Positive" and "Negative" for NST both descend from the start of the TEST section, thereby assuming that the sympathetic nervous system was promoted. No significant change was observed in the a wave. As for HF, from FIG. 25, it can be found that no significant change was observed in "Positive" but "Negative" significantly decreased. HF is taken as an index for activity of the parasympathetic nervous system, and increases and decreases in accordance with promotion and suppression of the parasympathetic nerves. Thus, it can be thought that "Negative" indicates that the parasympathetic nerves are suppressed. This coincides with the above-described interpretation in NST.

Figure 26:
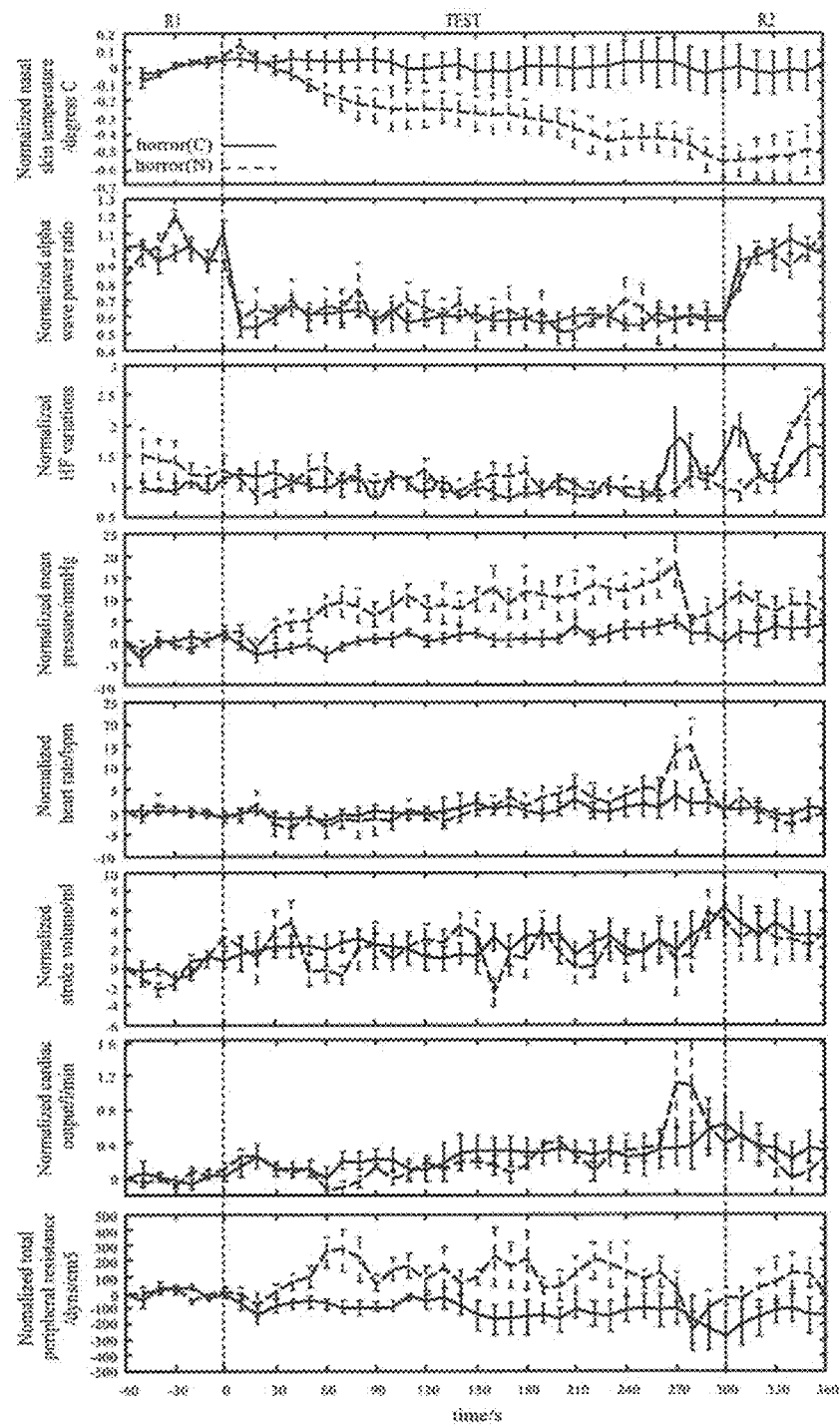
FIG. 26 is a graph illustrating time-series variations of physiological indices for "Horror (Concentration)" and "Horror (Notconcentration)" contents viewing.

Temporal variations of averages of physiological indices of horror video among the test subjects are illustrated in FIG. 26. In FIG. 26, N=14. From FIG. 26, since NST descends in "Horror (N)", it can be assumed that the sympathetic nerves were promoted. As for the a wave, no significant result was acquired on either side. It can be found that HF significantly decreases in "Horror (C)" and significantly increases in "Horror (N)". In "Horror (N)", HF did not coincide with the above-described interpretation in NST. This can be thought due to a difference in mechanism. As described further below, "Horror (N)" indicates passive coping characterized in an increase in TPR. As a result, it can be thought that the blood flow volume of the peripheral part decreases to decrease NST.

Figure 27:
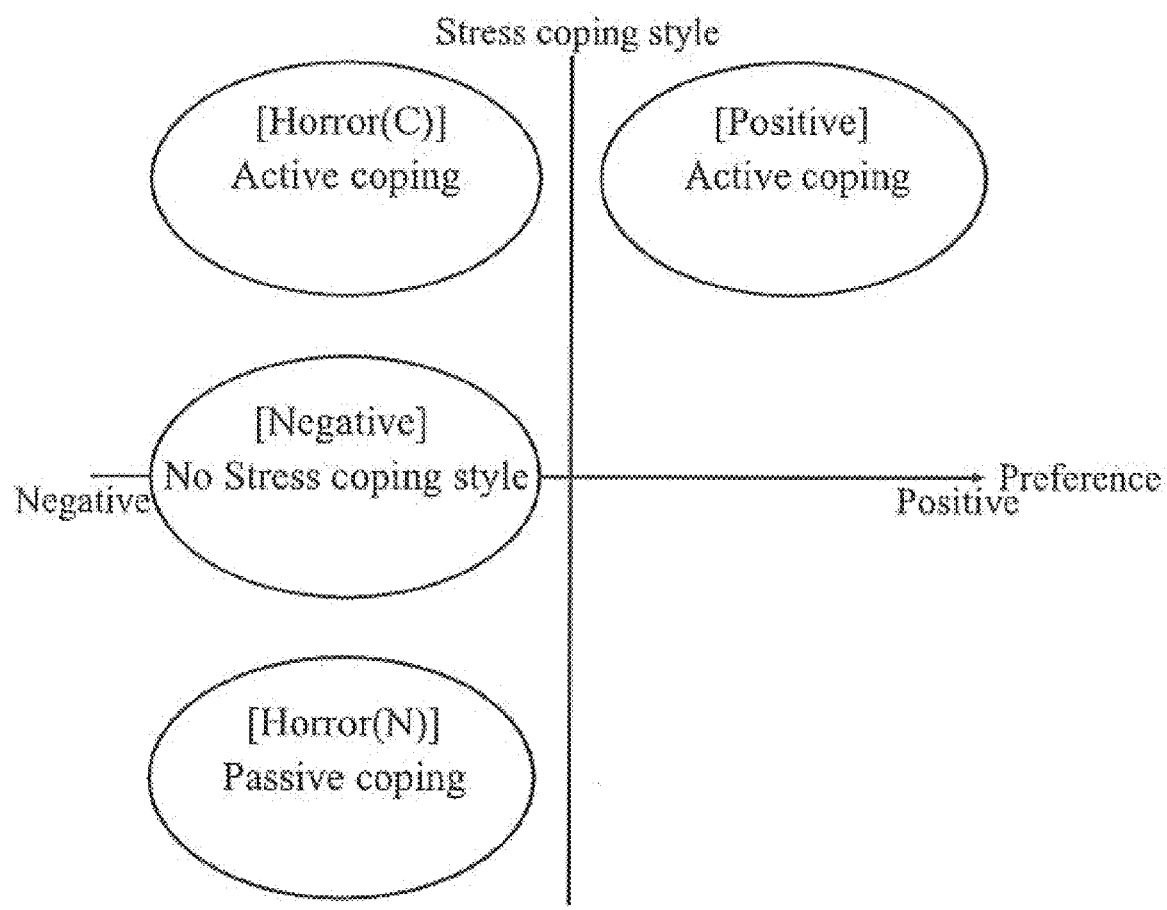
FIG. 27 is a graph illustrating relations between preferences and viewing modes for TV contents.

Next, "Positive", "Negative", "Horror (C)", and "Horror (N)" are categorized based on patterns of the sense of immersion and preference, and their hemodynamic responses are compared and studied. As a result, as in FIG. 27, these can be brought together with axes of the stress coping style and preference. In FIG. 27, N=14.

While the sense of immersion is high in both "Positive" and "Horror (C)", "Positive" indicates positive preference and "Horror (C)" indicates negative preference. However, an increase in MP, HR, SV, and CO and a decrease in TPR are observed in both. These are typical reactions of Pattern I (active coping) mainly due to an increase in myocardial contraction activity.

That is, in active coping, it has been revealed that the test subject is immersing in TV video contents irrespective of preference. Also, on the analogy of the results of the factor extraction experiment, test subjects with high preference also for horror video in the physiological measurement test have a high sense of immersion, and are expected to be positioned in an upper-right region of FIG. 27, but there were no relevant test subject. On the other hand, in both "Negative" and "Horror (N)", the sense of immersion and preference are low. However, their physiological responses are different. That is, in "Negative", while a decrease in TPR and HR was observed, no change was observed in MP. This can be considered as being neither active coping nor passive coping and being no stress coping. Note that N=14 in FIG. 27.

By contrast, in "Horror (N)", while no significant variation is present in HR, significant increases in TPR and MP are characteristic. These are typical reactions of Pattern II (passive coping) mainly due to an increase in MP due to an increase in peripheral vascular contraction. From this, it has been revealed that, when no stress coping is presented, while preference is normally low and the test subject is not immersed in TV video contents, passive coping is present for horror video. That is, it has been revealed that the viewing mode is not defined only by preference in TV video and viewing modes can be classified by stress coping styles.

4. Summary

In this study, physiological and psychological measurements were performed at the time of viewing video contents with different preferences, and classification of viewing modes by physiologically-based stress coping styles was tried. Hemodynamic parameters (MP, HR, SV, CO, TPR) were measured as indices of the cardiovascular system, an a-wave power spectrum in EEG was measured as an index of the central nervous system, and a nasal skin temperature and cardiac variation HF components were measured as indices of the autonomic nervous system. Including preferences in video simultaneously measured and a psychological questionnaire survey, statistical analyses regarding physiological and psychological states were performed, and physiological and psychological effects at the time of viewing video contents were quantitatively evaluated.

As a result, since classification by psychological indices regarding preference in this study has not been evaluated at all in prior studies, by combining stress copings and preferences of this study, new classification for television viewing was acquired. In conclusion, TV video indicates "Positive" and "Horror (C)" at the time of active coping, TV video indicates "Horror (N)" at the time of passive coping, and TV video indicates "Negative" at the time of no stress coping. That is, it has been revealed that, although the viewing mode cannot be determined only by preference in TV video, the viewing mode can be determined by the stress response with the hemodynamic parameter.

REFERENCE DOCUMENTS (1) Akihiro Hirata, Emi Morofuji, Hiroshi Aramaki: "The present state of TV viewing and media use (part 2) From the 2010 public opinion survey "the Japanese and television"", NHK monthly report on broadcast research, pp. 2-27 (2010)
(2) Hiroshi Aramaki, Tomoko Masuda, Sachiko Nakano: How Television Faces Twenties", NHK monthly report on broadcast research, pp. 2-21 (2008)
(3) Yuko Siki, You Murakami, and Yuiko Huzita: "Television viewing and simultaneous use of new media: an ethnographic study of young people in Japan", Institute for Media and Communication Research, Keio University, Vol. 59, No. 1, pp. 131-140 (2009)
(4) Shusaku Nomura, Yoshimasa Kurosawa, Nobuyuki Ogawa, C. M. Althaff Irfan, Kuniaki Yajima, Santoso Handri, Takao Yamagishi, Katsuko Nakahira, Yoshimi Fukumura: "Psyiological Evaluation of a student in E-learning Sessions by Hemodynamic Response", IEEJ Trans. EIS, Vol. 131, No. 1, pp. 146-151 (2011)
(5) Takuya Watanuki, Akio Nozawa: "Visualization of a feeling of concentration for TV contents", Bulletin of Institute of Electrical and Electronic Engineers of measurement, Vol. IM-12, No. 63, pp. 19-25 (2012)
(6) Mori Kurokawa, Chihiro Ono, Youichi Motomura, Hideki Asoh, and Akito Sakurai: "Empirical Analysis of User Preference Models for Movie Recommendation", IEIC Technical Report. NC. neurocomputing, Vol. 104, No. 759, pp. 77-82 (2005)
(7) Yukihiro Sawada: "Hemodynamic Reaction, New Physiopsychology Vol. I (edited by Kiyoshi Fujisawa, Shouji Kakinoki, Katsuo Yamazaki), Kitaohji Shobo Co., Ltd., Chapter 10, p. 187 (1998)
(8) J. A. Russell: "A circumplex model of affect", J. Personality and Social Psychology, Vol. 39, pp. 1161-1178 (1980)

<Experiment Example 3>

1. Gist of Experiment

In recent years, digital multichannel has been advanced in television broadcasting. However, with widespread of small-sized and sophisticated information communication equipment due to the recent advance of IT technologies and with development of information network environments, detachment from television as entertainment has accelerated and the reason for viewing television has been diversified. Hirata et al. cited, as reasons for viewing television, "to know events and movement in society", "to mitigate fatigue or relax", "to deepen and widen relationships with people" and so forth[1]. Also, not only in the reason for viewing television but also in the viewing mode, due to detachment from television, viewing has been changed to weakly-involved viewing such as an vague viewing attitude and weakened viewing habit[2]. Siki et al. cited viewing modes such as "dedicated viewing" of viewing television in a concentrated manner, "doing-another-thing viewing" of viewing in parallel with other life activities such as household chores, eating and drinking, studying, and so forth, and "vague viewing" of viewing various programs in an unplanned manner while zapping[3]. In this manner, it has been revealed that the viewing mode is varied and is transformed due to factors such as time, venue, feeling, and so forth.

However, most studies of determining these viewing modes use an opinion poll or a psychological response such as post introspective evaluation, and no study of classifying viewing modes by using a physical response. Since video and audio of television are audiovisual stimulations of the living body, they themselves are regarded as stressors. A stressor promotes the living body to perform stress coping, and brings a physiological/psychological change as a stress response.

If various television contents are regarded as stressors, their physiological stress response is expected to vary depending on coping with the contents, that is, the viewing mode. Nomura et al. classify coping modes with e-learning contents based on a cardiovascular-system index[4].

Hence, so far, classification of the viewing modes and preferences in TV video contents by the indices of the cardiovascular system has been tried[5]. Also, studies have been made not only on classification but also construction of an estimated model.

Kurokawa et al. constructed a user-preference model with respect to video contents by using naive Bayes, a decision tree, a Bayesian network, and a neural network and extracted prediction accuracy and important variables with respect to contents evaluation[6]. However, this study is directed to also a model using only a psychological response, and no study has been made in which an estimated model for preference and viewing modes is constructed by using a physiological response.

As a result of the studies so far, a possibility is suggested that the physiological and psychological states of television viewers such as preference and immersion in contents can be classified by a stress coping style based on the hemodynamic parameter and the heart rate. Hence, an object of this study is to make an experimental consideration on the above-described estimation of the physiological and psychological states of viewers regarding television viewing by indices of the cardiovascular system. Feature vectors were extracted from the indices of the cardiovascular system, and an estimated model of each of preference, viewing mode, and excitement-calm in television video contents was created and evaluated.

2. Experiment

Cardiovascular system measurements were performed by a continuous blood-pressure meter at the time of viewing TV video contents. Thereafter, by performing pattern recognition by using a hierarchical neural network based on hemodynamic parameters, preference, a viewing mode, and excitement-calm were estimated at the time of viewing TV video contents.

<2.1> Experiment Procedure

Figure 28:
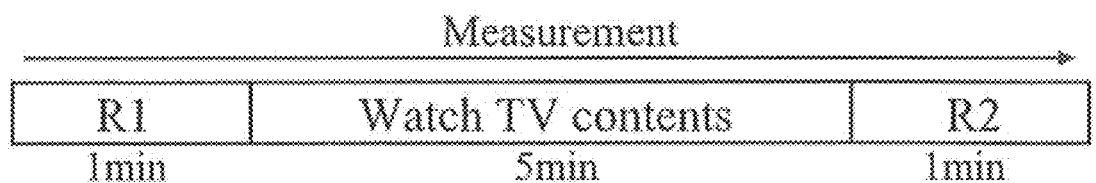
FIG. 28 is a conceptual diagram illustrating an experiment protocol of Experiment Example 3.

As illustrated in FIG. 28, this experiment is configured of five-minute video viewing and one-minute resting-closed-eyes states R1 and R2 before and after viewing. Preference and a sense of immersion in each of the video contents were evaluated by Visual Analogue Scale (hereinafter abbreviated as VAS) before and after video viewing and a sense-of-immersion survey after video viewing. Also, during video viewing, fluctuations in subjective excitement-calm being felt by the test subject on a real-time basis were recorded.

<2.2> Experiment Conditions

Test subjects are fourteen healthy students (ages: 19-22; average age: 21.4; seven males; and seven females) enrolled in Japanese universities. To the test subjects, the details, purpose, and investigation target of the experiment were sufficiently described in advance orally and in writing, and a consent to cooperate the experiment was confirmed with his/her signature. Measurements were performed in a shielded room at a room temperature of 26.0±1.6° C. without convection. To switch video contents and check a physiological measurement situation, one person performing the experiment attended in the same room. To acclimate the body surface temperature to the room temperature, the experiment was performed after the lapse of twenty minutes or more from the entry of the test subject into the room.

Each test subject being seated views, by using a liquid-crystal television (55 inches, HX850, BRAVIA, manufactured by SONY) set at a position 2 m ahead, contents of three types: video contents with positive preference and high immersion (hereinafter abbreviated as "Positive"), video contents with negative preference and low immersion (hereinafter abbreviated as "Negative"), and horror video indicating a specific result with low preference but its sense of immersion varied among individuals. The video contents were reproduced by a DVD player (SCPH-3900, manufactured by SONY).

<2.3> Measurement System

Figure 29:
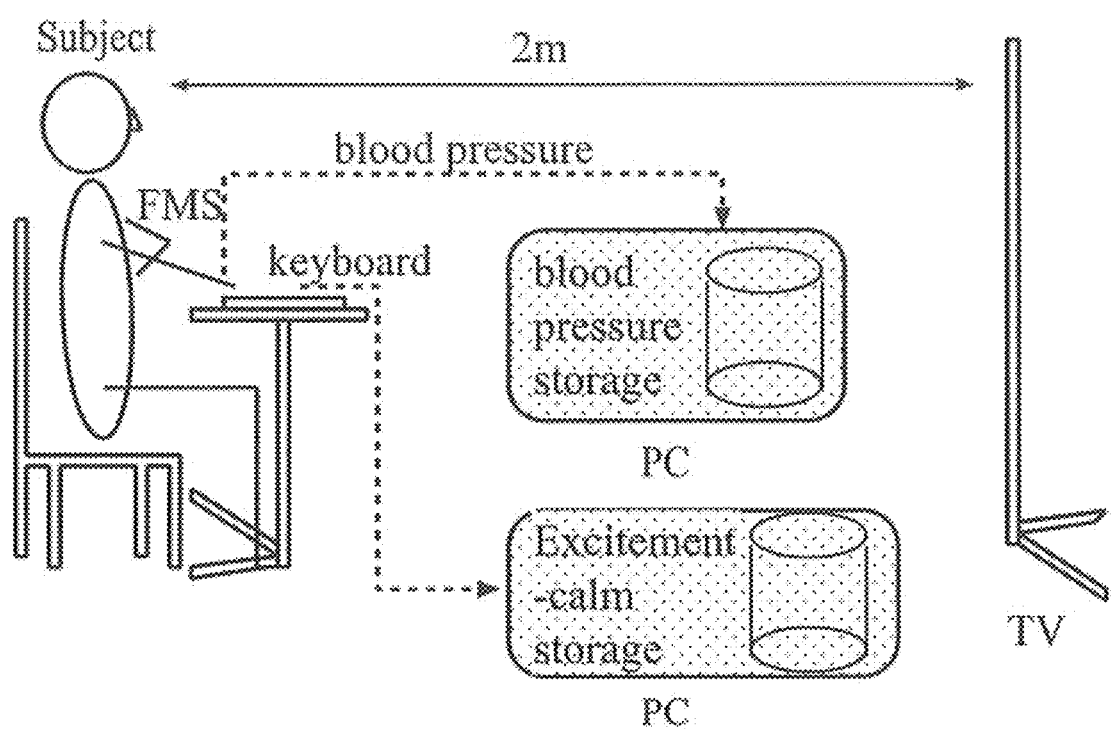
FIG. 29 is a conceptual diagram illustrating an experiment protocol.

A measurement system is illustrated in FIG. 29. Each test subject was seated, and had a continuous blood-pressure meter attached. As for the continuous blood-pressure meter (Finometer model 2, manufactured by Finapres Medical Systems B. V.), its cuff was attached to the second joint of the middle finger of the left arm, and recordings were made on a PC at a sampling frequency of 200 Hz. Also, a keyboard (K270, manufactured by Logicool) was set in front of the test subject, and sequential and relative excitement-calm was recorded with up and down keys on the keyboard on a real-time basis by using software for inputting fluctuations in subjective excitement-calm being felt by the test subject.

<2-4> Evaluation Method

Physiological indices were a mean blood pressure (hereinafter abbreviated as MP), a heart rate (hereinafter abbreviated as HR), a stroke volume (hereinafter abbreviated as SV), a cardiac output (hereinafter abbreviated as CO), and a total peripheral resistance (hereinafter abbreviated as TPR). Hemodynamic parameters (MP, HR, SV, CO, and TPR) are known to indicate a characteristic reaction pattern (Pattern I, Pattern II) in response to external stress, and are an important concept to understand a physiological reaction of the cardiovascular system against stress. Specifically, Pattern I is characterized in promotion of myocardial contraction activity and an increase in blood volume to the skeletal muscle due to vasodilation. This can be said as energy-consumption-type reaction (active coping), so to speak. On the other hand, Pattern II is characterized in contraction of peripheral vessels, and also the heart rate generally decreases. This can be said as energy-saving-type reaction (passive coping)[7]. MP, HR, SV, CO, and TPR are normalized by taking the baseline of the R1 section as 0.

Also, as psychological indices, intensities of subjective sense of four types, that is, "sense of awakening", "comfort/discomfort", "vitality", and "preference", were measured before the start and at the end of the experiment by using VAS. "Comfort/discomfort" and "sense of awakening" were selected as items for psychological evaluation in this study as basic components of Russell's emotion dualism[8]. In VAS, by arranging paired adjectives on both ends of a line segment and prompting the test subject to check any position on the line segment, psychophysical quantity of the test subject can be measured. As for words arranged on both ends of the scale, "very sleepy" to "clearly awaken" for the sense of awakening, "very discomfortable" to "very comfortable" for comfort/discomfort, and "very tired" to "very vigorous" for vitality, and "really hate" to "really like" for preference were taken.

Each VAS was prepared on an independent paper sheet, and the test subject was taught to sequentially record in his/her own handwriting without recursive referencing. Furthermore, after the end of the experiment, the sense of immersion to video was measured with 5-point scale (1: not immersed at all to 5: considerably immersed). Note that, the paired t-test was used for a test of a difference before and after video viewing of each psychological index, and the Wilcoxon signed-rank test was used for the change amount in the entire TEST section of each physiological index. Excitement-calm was normalized with reference to a maximum value of integration.

For creation of a preference and a viewing mode classification model and derivation of a distinction rate, and creation of an excitement-calm estimated model for each test subject and derivation of an estimated value, pattern recognition by a hierarchical neural network was used.

Figure 31:
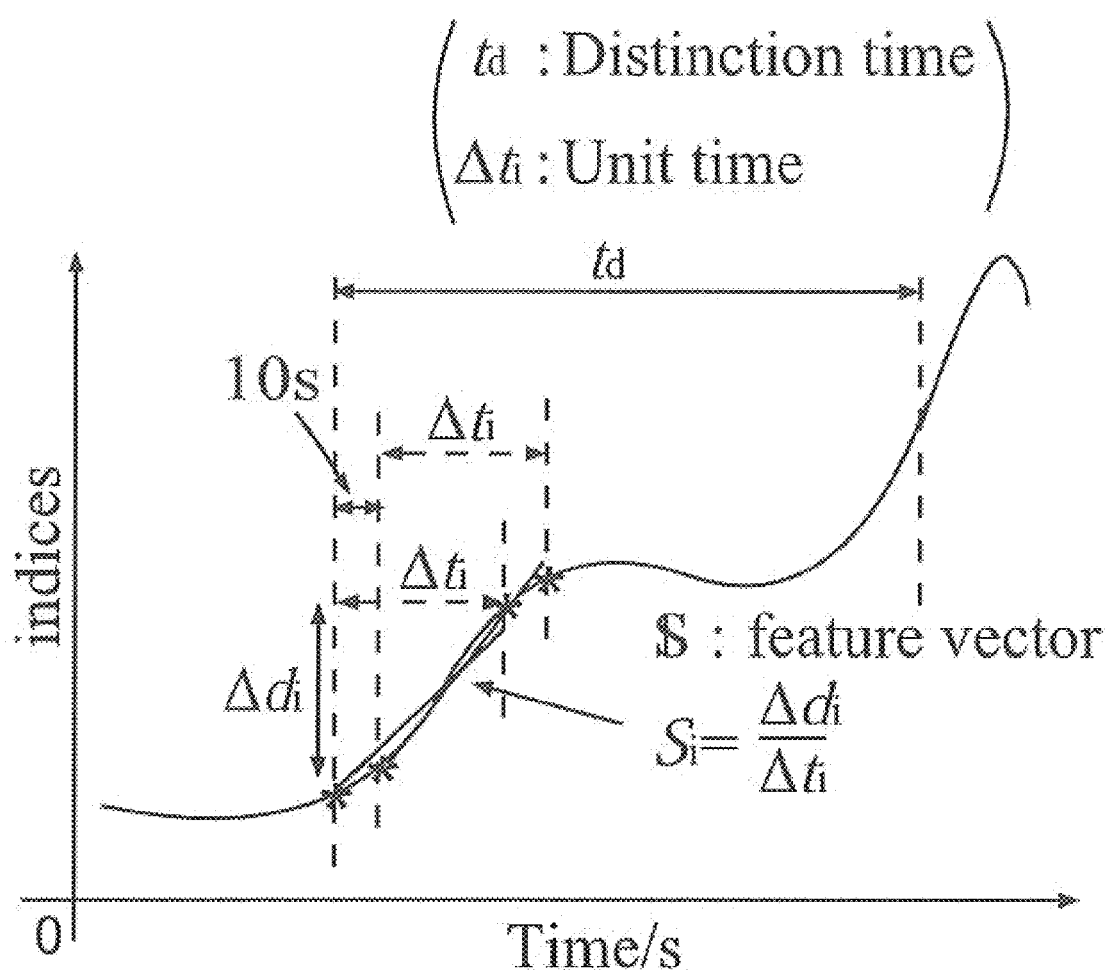
FIG. 31 is a graph illustrating a feature vector extraction method.

The structure of the hierarchical neural network is illustrated in FIG. 30. The back propagation method was taken as a learning rule, and a sigmoid function was taken as an output function. The hierarchy has three layers: an input layer, an intermediate layer, and an output layer. For model accuracy estimation, a cross-validation method was used. Also as illustrated in FIG. 31, for variations with time of each index, a distinction time ta is assumed. $t_d$ is 300 s during video viewing. In each model, in each feature value time series in the $t_d$ section, attention is paid to the slope per $\Delta t_i$, and a series of slopes for each 10 s interval is taken as a feature vector S. The number of elements of S is 30. In accordance with this, in this neural network, the number of elements in the input layer was taken as 30 and the number of elements in the intermediate layer was taken as 16.

<2-4-1> Preference Classification Model A heart rate was used as a feature value, and 10 s, 20 s, 30 s, 40 s, 50 s, and 60 s were considered as $\Delta t_i$. The entire learning data had twenty-eight patterns with each preference (Positive, Negative) of fourteen test subjects. Among these, twenty-seven patterns were taken as learning data and the remaining one pattern as unknown data, and accuracy of a preference classification model was evaluated. After the feature vectors S at the time of "Positive" and "Negative" were learned, unknown data is inputted, thereby evaluating accuracy of the preference classification model. The output layer has two elements: "Positive" and "Negative".

<2.4.2> Viewing Mode Classification Model A hemodynamic parameter was used as a feature value, and 10 s, 20 s, 30 s, 40 s, 50 s, and 60 s were considered as $\Delta t_i$. The entire learning data had forty-two patterns with each stress coping style (active coping, passive coping, no stress coping) of fourteen test subjects. Among these, forty-one patterns were taken as learning data and the remaining one pattern as unknown data, and accuracy of a preference classification model was evaluated. The output layer has three elements: active coping, passive coping, no stress coping.

<2-4.3> Excitement-Calm Estimated Model A hemodynamic parameter was used as a feature value, and $\Delta t_i$ was set at 30 s. The entire learning data had twenty-eight patterns with excitement-calm values in each preference (Positive, Negative) of fourteen test subjects. Among these, twenty-seven patterns were taken as learning data and the remaining one pattern as unknown data, and accuracy of a preference classification model was evaluated. The output layer has one element: an excitement-calm value.

<2.5> Results and Discussion In VAS, a difference in averages of all test subjects between pre-video-viewing and post-video-viewing for each mood scale is illustrated in FIG. 32 (+: p<0.1, *: p<0.05, **: p<0.01). In FIG. 32, N=14. From FIG. 32, as for horror video stimulation, all test subjects had low preference. Thus, in evaluation of the sense of immersion in five stages after horror video viewing, 4 or 5 was classified as Horror (Concentration) (hereinafter abbreviated as "Horror (C)") and 1 or 2 as Horror (No-Concentration) (hereinafter abbreviated as "Horror (N)"). The results hereinafter are represented as classified into "Positive", "Negative", "Horror (C)", and "Horror (N)". Also, the number of persons with "Horror (C)" is ten, and the number of persons with "Horror (N)" is four.

As for MP, HR, SV, CO, and TPR, significance probability p of the Wilcoxon signed-rank test regarding deviation from the baseline in the entire TEST section is illustrated in FIG. 33 (+: p<0.1; *: p<0.05; **: p<0.01). In the table, P refers to a positive response and N refers to a negative response to each index. In FIG. 33, N=14.

From FIG. 33, viewing modes at the time of TV video viewing are classified. While the sense of immersion is high in both "Positive" and "Horror (C)", "Positive" indicates positive preference and "Horror (C)" indicates negative preference. However, an increase in MR, HR, SV, and CO and a decrease in TPR are observed in both. These are typical reactions of Pattern I (active coping) mainly due to an increase in myocardial contraction activity. That is, in active coping, it has been revealed that the test subject is immersing in TV video contents irrespective of preference.

On the other hand, the sense of immersion and preference are low in "Negative" and "Horror (N)". However, their physiological response varies. That is, in "Negative", while a decrease in TPR and HR was observed, no change was observed in MP. This is because of neither active coping nor passive coping, but no stress coping. By contrast, in "Horror (N)", while no significant variation is present in HR, significant increases in TPR and MP are characteristic. These are typical reactions of Pattern II (passive coping) mainly due to an increase in MP due to an increase in peripheral vascular contraction.

From this, it has been revealed that when no stress coping is presented, while preference is normally low and the test subject is not immersed in TV video contents, passive coping is present for horror video. That is, it has been revealed that the viewing mode is not defined only by preference in TV video and viewing modes can be classified by stress coping styles. Also in FIG. 33, HR significantly increased in "Positive" and significantly decreased in "Negative".

Figure 35:
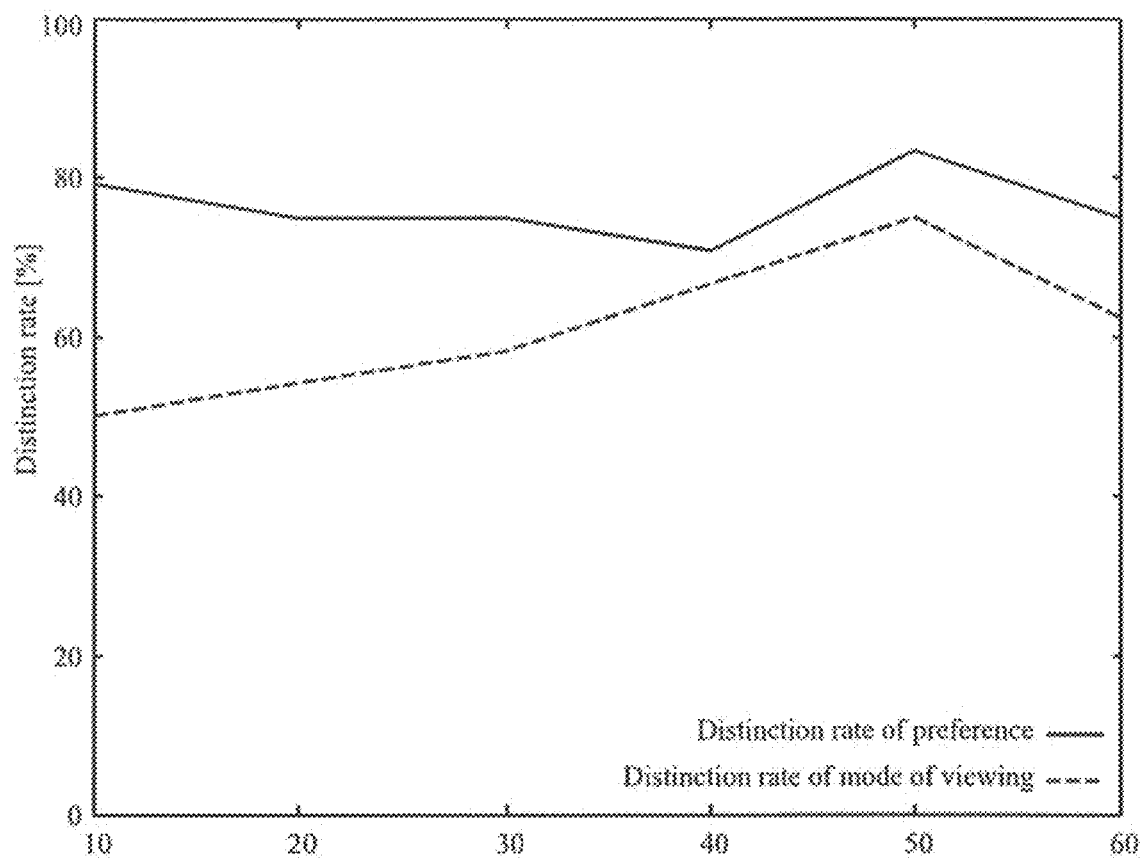
FIG. 35 is a graph illustrating a positive distinction rate of preference and a viewing mode for TV contents.

Next, from the estimated model constructed by using a neural network, the results of distinction rates when distinctions as to preference and the viewing mode were performed are illustrated in FIG. 34 and FIG. 35. In FIG. 34 and FIG. 35, when $\Delta t_i$ is 50 s, the positive distinction rate of preference is 83.3% and the positive distinction rate of the viewing mode is 75%, and these positive distinction rates are higher than those for other $\Delta t_i$.

Figure 36:
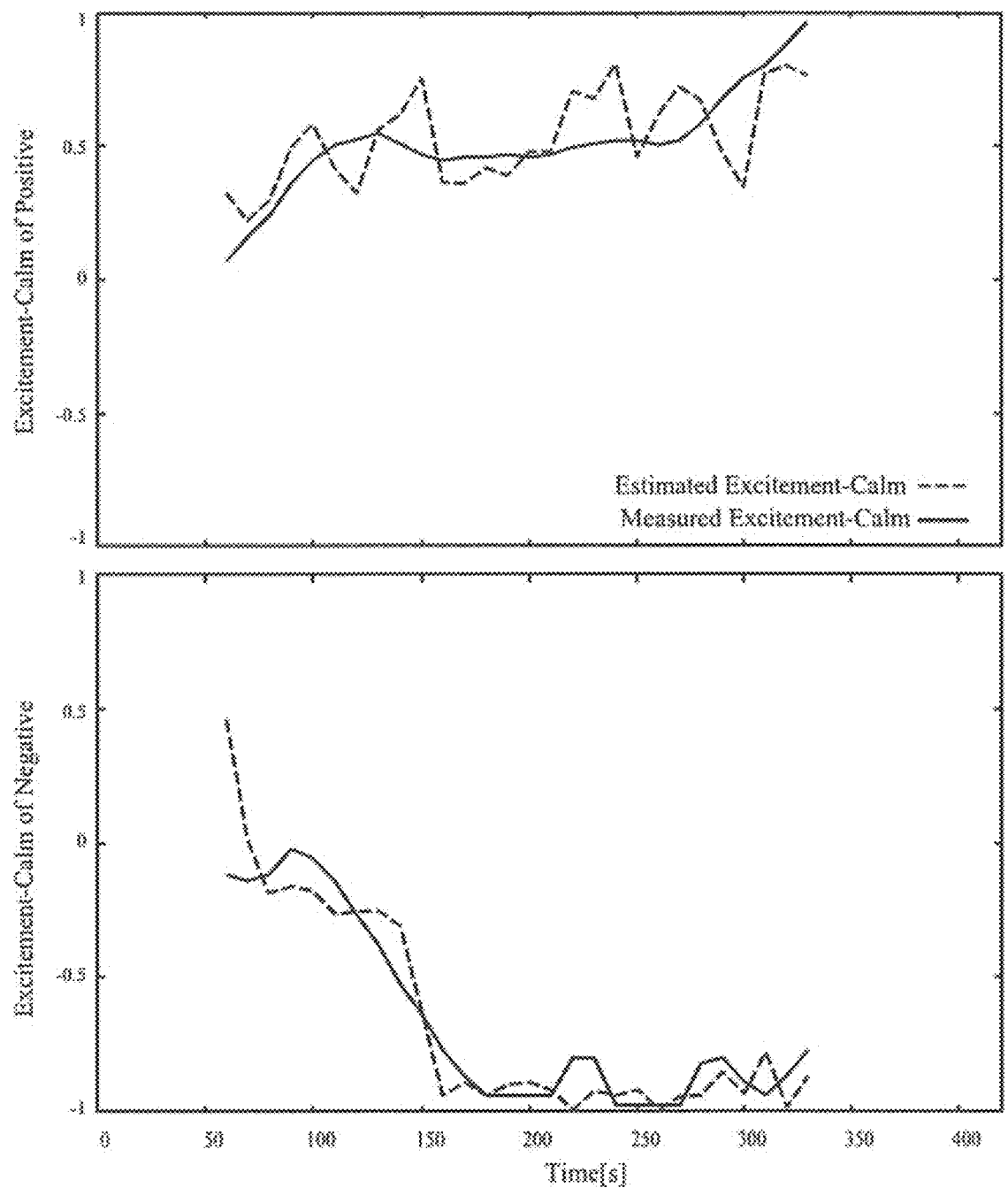
FIG. 36 is a graph illustrating temporal variations of a measured value and an estimated value in "Excitement-Calm" state.

Also, measured excitement-calm and estimated excitement-calm when excitement-calm estimation was performed are illustrated in FIG. 36.

FIG. 36 illustrates the results for the test subject A with a difference between measured excitement-calm and estimated excitement-calm is minimum. In "Positive" on an upper side of FIG. 36, as measured excitement-calm increases, estimated excitement-calm also increases.

Figure 37:
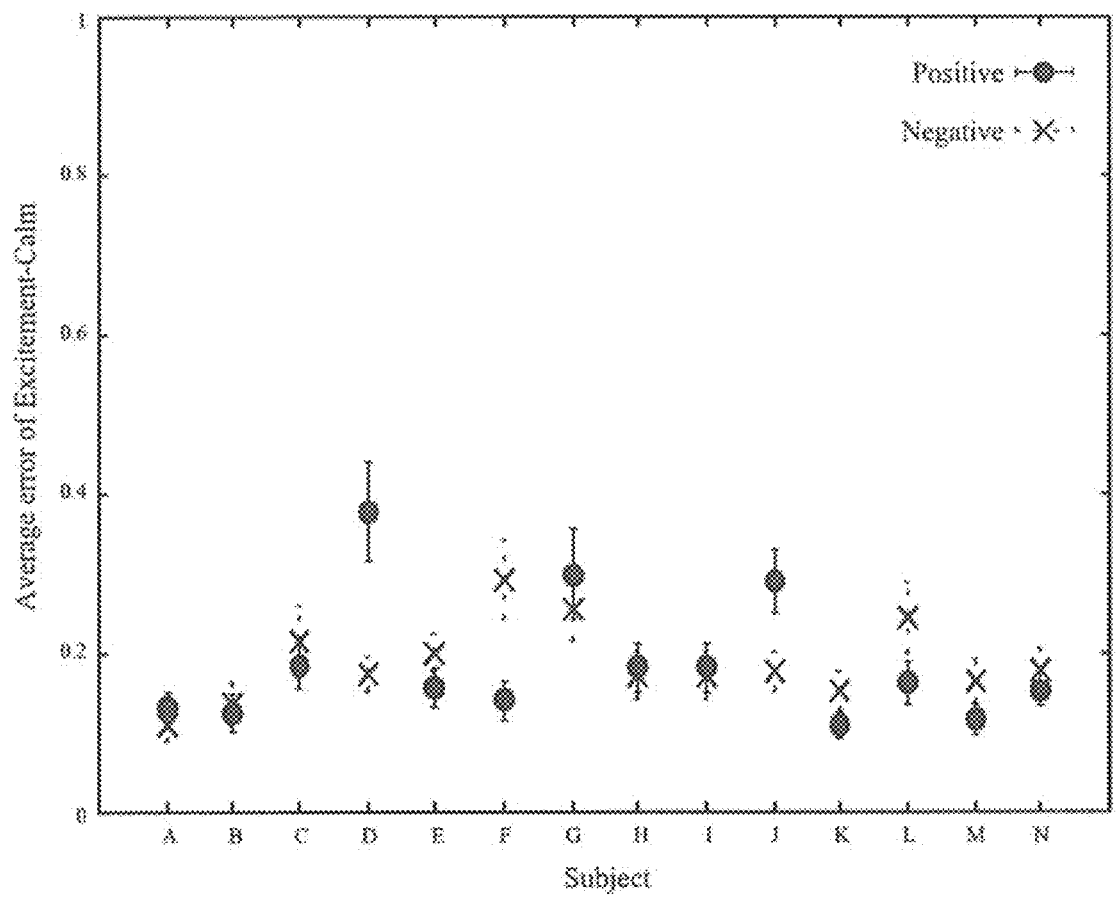
FIG. 37 is a graph illustrating an estimated error in "Excitement-Calm" state.
Figure 38:
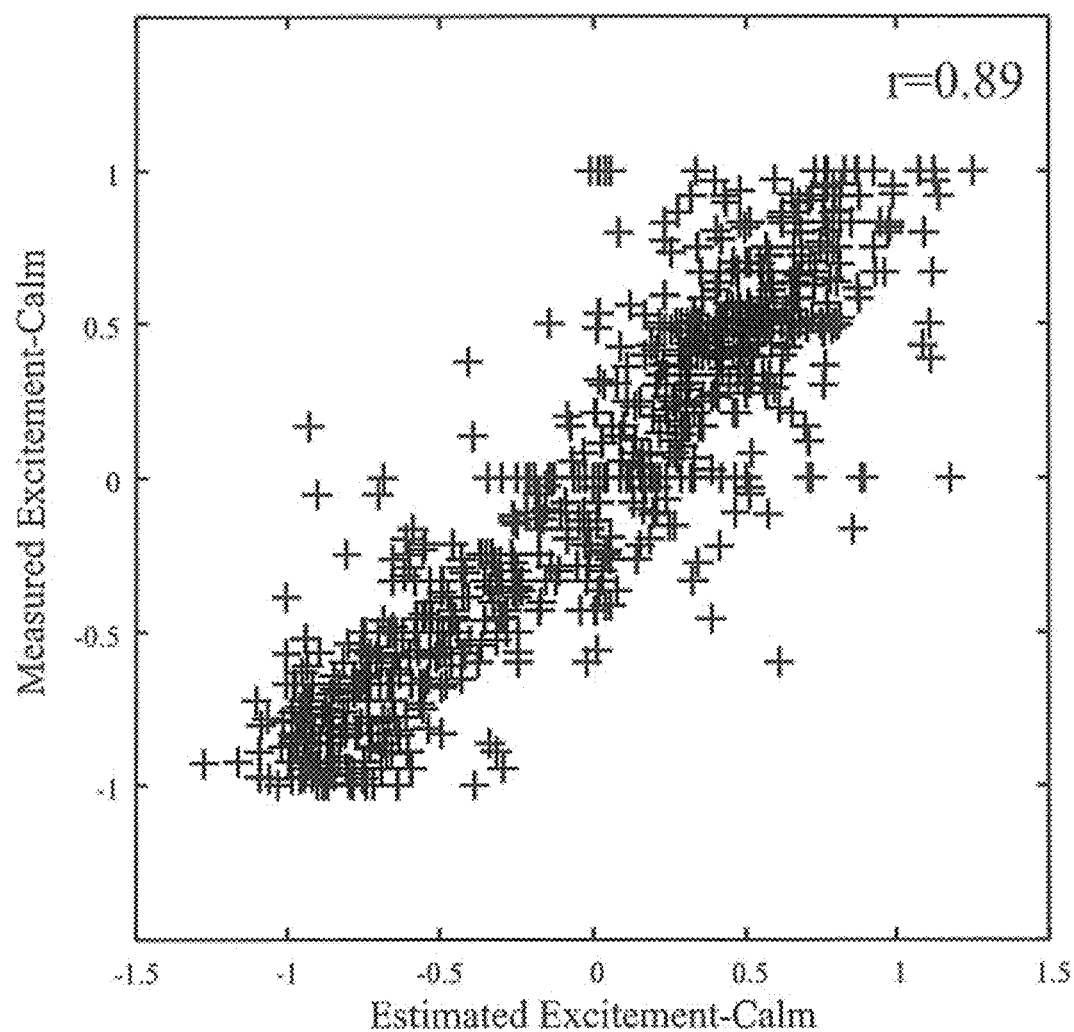
FIG. 38 is a graph illustrating a relation between a measured value and an estimated value in "Excitement-Calm" state.

Also, in "Negative" on a lower side of FIG. 36, as measured excitement-calm decreases, estimated excitement-calm also decreases. Next, an average error of each test subject when an absolute value of a difference between measured excitement-calm and estimated excitement-calm is taken as an error is illustrated in FIG. 37. In FIG. 37, the average error in "Positive" is 0.10 to 0.37, the average error in "Negative" is 0.11 to 0.29, the average error on the average among all test subjects is 0.17. That is, estimated excitement-calm was estimated with an error on the order of 17% on average. Also, a drawing illustrating a relation between a series of measured excitement-calm and estimated excitement-calm taken for each 10 s interval for all test subjects is illustrated in FIG. 38. In FIG. 38, a high correlation was acquired, with a correlation coefficient of 0.89. Also, from FIG. 38, it can be found that a distribution of measured excitement-calm and estimated excitement-calm is approximately uniform irrespective of the magnitude of the value.

3. Summary

In this study, for the purpose of estimating a viewing mode, preference, and excitement-calm in television video contents by using a neural network, feature vectors were extracted from the indices of the cardiovascular system, and estimated models of preference, viewing mode, and excitement-calm at the time of viewing television video contents were created and evaluated.

As a result, classification can be made as "Positive" with positive preference and high immersion, and "Horror (C)" with negative preference and high immersion being active coping, "Horror (N)" with no-preference and high immersion being passive coping, "Negative" with negative preference and low immersion being no stress coping. Furthermore, the heart rate significantly varied between "Positive" and "Negative", and the result in accordance with general characteristics in cardiac response were acquired. Also, when preference and the viewing mode were determined by using the estimated models, the positive distinction rate of preference was 83.3% and the positive distinction rate of the viewing mode was 75%, at maximum.

As a result of estimation of excitement-calm for each test subject, the average error between measured excitement-calm and estimated excitement-calm was 10% to 37% in "Positive" and 11% to 29% in "Negative", and an average among all test subjects was 17%. Furthermore, a strong positive correlation was observed between measured excitement-calm and estimated excitement-calm, with a correction coefficient of 0.89. From above, a possibility is suggested that preference, the viewing mode, and excitement-calm at the time of viewing television video contents can be estimated by the hemodynamic parameter and the heart rate. In the future, with other physiological indices or by comparing and considering with other discriminators, a further improvement in accuracy is planned to be sought.

REFERENCE DOCUMENTS (1) Toru Nishigaki: "Will television revive by the Internet?", Commercial broadcasting monthly, 2001
(2) Norimichi Fujiwara, Yumiko Saito, "Opinion Poll Report: Evaluation and Expectation on Television—From Results of "Role of Television" Survey-", NHK monthly report on broadcast research, June issue, pp. 2-15 (1989)
(3) Hiroaki Ohnogi: "Chapter 9, Television Viewing Attitude of Female University Students and Several Factors: From Personality Characteristics, Interests on Program Contents, and Preliminary Investigations Regarding Purpose of Television Viewing (Studies on Program Analysis and Viewing learning Activity: Aiming at Development of Taxonomy of Broadcast Educational Programs)", Study Report, Vol. 18, pp. 153-172 (1990)
(4) Yasushi Takahashi, Shackleton John: "Recommendation Models of Television Program Genre, Based on Survey and Analysis of Behaviour in Watching Television: Toward Human Content Interface Design (2)", Bulletin of Japanese Society for Science of Design, Vol. 46, No. 133, pp. 71-80 (1999)
(5) Yumiko Tomomune, Yumiko Hara "Television as "Device Making Time Comfortable"-Relation between Viewing Attitude and Programs all becoming Variety Shows-", Monthly Report on Broadcast Research, Vo. 51, pp. 2-17 (2001)
(6) Shusaku Nomura, Yoshimasa Kurosawa, Nobuyuki Ogawa, C. M. Althaff Irfan, Kuniaki Yajima, Santoso Handri, Takao Yamagishi, Katsuko Nakahira, and Yoshimi Fukumura: "Psysiological Evaluation of a student in E-learning Sessions by Hemodynamic Response", IEEJ Trans. EIS, Vol. 131, No. 1, pp. 146-151 (2011)
(7) Yukihiro Sawada: "Hemodynamic Reaction, New Physiopsychology Vol. I (edited by Kiyoshi Fujisawa, Shouji Kakinoki, Katsuo Yamazaki), Kitaohji Shobo Co., Ltd., Chapter 10, p. 187 (1998)
(8) A. Michimori: "Relationship between the alpha attenuation test, subjective sleepiness and performance test", 10th Symposium on Human Interface, Vol. 10, No. 1413, pp. 233-236 (1992)
(9) Masaharu Terasaki, Youichi Kishimoto, Aito Koga: "Construction of a multiple mood scale", The Japanese Journal of Psychology, Vol. 62, No. 6, pp. 350-356 (1992)
(10) J. A. Russell: "A circumplex model of affect", J. Personality and Social Psychology, Vol. 39, pp. 1161-1178 (1980)

INDUSTRIAL APPLICABILITY

The stress coping style determination system of the present invention can qualitatively analyze stress of the test subject in a non-contact state, and thus has possibilities of use in wide-range technical fields such as means for grasping a stress state of workers working in a factory or the like, means for grasping a stress state of a driver driving an automobile, means for grasping a stress state of students during attending a class, and so forth.

REFERENCE SIGNS LIST 100 stress coping style determination system
110 biological information acquiring device (biological information acquiring part)
120 determination device (determining part)
121 determination-purpose feature value storage part
122 specific region reaction detecting part
123 response pattern determining part
130 learning device (machine learning part)
131 learning data storage part
132 feature value extracting part
133 feature value learning part
134 learned model
P test subject
IF facial image
S1 determination-purpose feature value storing process (determination-purpose feature value storing step)
S2 specific region reaction detecting process (specific region reaction detecting step)
S3 response pattern determining process (response pattern determining step)
S11 learning data storing process (learning data storing step)
S12 feature value extracting process (feature value extracting step)
S13 feature value learning process (feature value learning step)
S21 clustering process (clustering step)
S22 image extracting process (image extracting step)
S23 edge extracting process (edge extracting step)
S24 fractal analysis process (fractal analysis step)

The invention claimed is:
1. A stress coping style determination system, comprising:
a biological information acquiring part which acquires biological information of a test subject in a non-contact state; and
a determining part which determines a stress coping style of the test subject based on the biological information and a response pattern specified in advance, wherein
the response pattern is specified by a hemodynamic parameter and includes patterns for a plurality of stress coping styles from which the stress coping style is determined by the determining part.
2. The stress coping style determination system according to claim 1, wherein
the hemodynamic parameter includes a plurality of parameters among a mean blood pressure, a heart rate, a cardiac output, a stroke volume, and a total peripheral resistance.
3. The stress coping style determination system according to claim 1, wherein
the biological information is a facial image.

4. The stress coping style determination system according to claim 3, wherein
the facial image is a facial thermal image or a facial visible image.

5. The stress coping style determination system according to claim 1, wherein
the determining part determines the stress coping style of the test subject by observing a stress response of a specific region of a facial surface including in the facial image.

6. The stress coping style determination system according to claim 5, wherein
the response pattern includes patterns of three types: "active coping", "passive coping", and "no coping".

7. The stress coping style determination system according to claim 6, wherein
the determining part comprises a determination-purpose feature value storage part which has stored therein a spatial feature value corresponding to "active coping", a spatial feature value corresponding to "passive coping", and a spatial feature value corresponding to "no coping", and
the determining part determines that the stress coping style is any pattern among "active coping", "passive coping", and "no coping", based on the biological information and the respective spatial feature values stored in the determination-purpose feature value storage part.

8. The stress coping style determination system according to claim 7, wherein
the feature values stored in the determination-purpose feature value storage part are feature values extracted by a machine learning part, and
the machine learning part comprises:
a learning data storage part which has stored therein a plurality of learning-purpose facial images labelled so as to correspond to "active coping", "passive coping", and "no coping", respectively;
a feature value extracting part which extracts a spatial feature value of the facial image from the learning-purpose facial images by using a learned model; and
a feature value learning part which changes a network parameter of the learned model so that extraction accuracy of the spatial feature value by the feature value extracting part is enhanced, based on a relation between the extraction result by the feature value extracting part and a label provided to the learning-purpose facial image as an extraction target.

9. The stress coping style determination system according to claim 7, wherein
the spatial feature value is a fractal dimension calculated based on the facial image of the test subject.

10. A non-transitory computer medium storing computer executable code, which when executed by one or more processors, implements a method of determining the spatial feature value for the stress coping style determination system of claim 9, wherein
the method comprises:
a learning data storing step of storing a plurality of learning-purpose facial images labelled so as to correspond to "active coping", "passive coping", and "no coping", respectively;
a feature value extracting step of extracting a spatial feature value of the learning-purpose facial image by using a learned model; and
a learning step of changing a network parameter of the learned model so that extraction accuracy of the spatial feature value at the feature value extracting step is enhanced, based on a relation between the extraction result at the feature value extracting step and a label provided to the learning-purpose facial image as an extraction target, and
the determination-purpose feature value storing step is a step of storing the spatial feature value extracted at the feature value extracting step.

11. A non-transitory computer medium storing computer executable code, which when executed by one or more processors, implements a method of causing a computer to function as means of determining the stress coping style determination system of claim 1 of the test subject, the method comprising:
a determination-purpose feature value storing step of storing a spatial feature value corresponding to "active coping", a spatial feature value corresponding to "passive coping", and a spatial feature value corresponding to "no coping"; and
a determining step of determining whether the stress coping style of the test subject is any response pattern among "active coping", "passive coping", and "no coping", based on a facial image of the test subject and the respective spatial feature values stored at the determination-purpose feature value storing step, wherein
the response pattern is specified by the hemodynamic parameter.

12. The program non-transitory computer medium according to claim 11, wherein
the spatial feature value is a fractal dimension calculated based on the facial image of the test subject.

13. A stress coping style determination method, comprising:
a biological information acquiring step of acquiring biological information of a test subject in a non-contact state; and
a determining step of determining a stress coping style of the test subject based on the biological information and a response pattern specified in advance, wherein
the response pattern is specified by a hemodynamic parameter and includes patterns for a plurality of stress coping styles from which the stress coping style is determined by the determining step.

14. A learning device, comprising:
a learning data storage part which has stored therein a plurality of learning-purpose facial images labelled so as to each correspond to a response pattern specified by a hemodynamic parameter;
a feature value extracting part which extracts a spatial feature value of a facial image of a test subject from the learning-purpose facial images by using a learned model; and
a feature value learning part which changes a network parameter of the learned model so that extraction accuracy of the spatial feature value by the feature value extracting part is enhanced, based on a relation between the extraction result at the feature value extracting part and a label provided to the learning-purpose facial image as an extraction target.

15. The learning device according to claim 14, wherein
the spatial feature value is a fractal dimension calculated based on the facial image of the test subject.

16. A learning method of the learning device of claim 14, comprising:

a learning data storing step of storing the plurality of learning-purpose facial images labelled so as to each correspond to the response pattern specified by the hemodynamic parameter;

a feature value extracting step of extracting the spatial feature value of the facial image of the test subject from the learning-purpose facial images by using the learned model; and a feature value learning step of changing the network parameter of the learned model so that extraction accuracy of the spatial feature value by the feature value extracting step is enhanced, based on the relation between the extraction result at the feature value extracting step and the label provided to the learning-purpose facial image as the extraction target.

17. The learning method according to claim 16, wherein the spatial feature value is a fractal dimension calculated based on the facial image of the test subject.

18. A non-transitory computer medium storing computer executable code, which when executed by one or more processors, implements a method of learning the spatial feature value of the facial image of the test subject of the learning device of claim 14, the method comprising a learning data storing step of storing the plurality of learning-purpose facial images labelled so as to each correspond to the response pattern specified by the hemodynamic parameter;

a feature value extracting step of extracting the spatial feature value of the facial image of the test subject from the learning-purpose facial images by using the learned model; and a feature value learning step of changing the network parameter of the learned model so that extraction accuracy of the spatial feature value by the feature value extracting step is enhanced, based on the relation between the extraction result at the feature value extracting step and the label provided to the learning-purpose facial image as the extraction target.

19. The non-transitory computer medium according to claim 18, wherein the spatial feature value is a fractal dimension calculated based on the facial image of the test subject.

20. The learning device according to claim 14, wherein a learned model of the learning device is generated by machine-learning the spatial feature value of the facial image of the test subject by using the plurality of learning-purpose facial images labelled so as to each correspond to the response pattern specified by the hemodynamic parameter as teacher data.

21. The learning device according to claim 20, wherein the spatial feature value is a fractal dimension calculated based on the facial image of the test subject.

* * * * *